(12) United States Patent
Bickley et al.

(10) Patent No.: US 7,967,851 B2
(45) Date of Patent: Jun. 28, 2011

(54) METHOD AND APPARATUS FOR SECURING AN OBJECT TO BONE

(76) Inventors: Barry T. Bickley, North Andover, MA (US); Aldo M. Zovich, East Hampton, CT (US); Richard E. Zovich, Kensington, CT (US)

(*) Notice: Subject to any disclaimer, the term of this patent is extended or adjusted under 35 U.S.C. 154(b) by 291 days.

(21) Appl. No.: 12/148,845

(22) Filed: Apr. 23, 2008

(65) Prior Publication Data
US 2009/0082814 A1 Mar. 26, 2009

Related U.S. Application Data

(63) Continuation-in-part of application No. 10/544,379, filed as application No. PCT/US2004/014640 on May 10, 2004.

(60) Provisional application No. 60/468,829, filed on May 8, 2003, provisional application No. 60/925,729, filed on Apr. 23, 2007.

(51) Int. Cl.
*A61B 17/04* (2006.01)
*A61B 17/86* (2006.01)
*A61F 2/08* (2006.01)

(52) U.S. Cl. ........ 606/313; 606/300; 606/309; 606/286; 606/280

(58) Field of Classification Search ............... 606/70, 606/71, 300–321, 60, 61, 246, 264–279, 606/280–297; 411/151, 158, 161, 294
See application file for complete search history.

(56) References Cited

U.S. PATENT DOCUMENTS
1,752,752 A 4/1930 Ogden
2,307,179 A 1/1943 Whitehead
(Continued)

FOREIGN PATENT DOCUMENTS
CH 645 168 A5 9/1984
(Continued)

OTHER PUBLICATIONS

Joseph H. Sklar, M.D.; "Technique for Tibial Fixation of ACL Grafts;" Innovasive Devices; 1999.
(Continued)

*Primary Examiner* — Eduardo C Robert
*Assistant Examiner* — Christina Negrelli
(74) *Attorney, Agent, or Firm* — Pandiscio & Pandiscio

(57) ABSTRACT

A surgical system comprising:
an object to be secured to bone, the object comprising an opening extending therethrough; and
a sleeve/expander construction for securing the object to bone, the sleeve/expander construction comprising:
a sleeve adapted for positioning through the opening in the object and into the bone, the sleeve comprising:
a shank having a distal end and a proximal end and an opening extending from the distal end to the proximal end, wherein the opening narrows toward the distal end of the shank, and further wherein the distal end of the shank is slit so as to form a plurality of radially-expandable segments; and
an enlarged head formed at the proximal end of the shank, the enlarged head being formed so as to be radially-expandable; and
an expander adapted for positioning through the opening in the sleeve, the expander being sized so as to (i) radially expand the distal end of the sleeve so that the sleeve is secured to the bone, and (ii) radially expand the enlarged head of the sleeve so that the sleeve is secured to the object, whereby to secure the object to the bone.

22 Claims, 36 Drawing Sheets

U.S. PATENT DOCUMENTS

| | | | |
|---|---|---|---|
| 2,381,050 A | 8/1945 | Hardinge | |
| 3,174,387 A | 3/1965 | Fischer | |
| 3,232,163 A | 2/1966 | Croessant | |
| 3,473,222 A | 10/1969 | Kester | |
| 3,896,504 A | 7/1975 | Fischer | |
| 4,201,531 A | 5/1980 | Schurman | |
| 4,276,806 A | 7/1981 | Morel | |
| 4,312,612 A | 1/1982 | Thompson | |
| 4,388,921 A | 6/1983 | Sutter et al. | |
| 4,484,570 A | 11/1984 | Sutter et al. | |
| 4,601,625 A | 7/1986 | Ernst et al. | |
| 4,611,581 A | 9/1986 | Steffee | |
| 4,716,893 A | 1/1988 | Fischer et al. | |
| 5,084,050 A | 1/1992 | Draenert | |
| 5,224,805 A | 7/1993 | Moretti et al. | |
| 5,324,292 A | 6/1994 | Meyers | |
| 5,356,435 A | 10/1994 | Thein | |
| 5,601,558 A | 2/1997 | Torrie et al. | |
| 5,713,904 A | 2/1998 | Errico et al. | |
| 5,716,359 A | 2/1998 | Ojima et al. | |
| 5,720,753 A | 2/1998 | Sander et al. | |
| 5,725,529 A | 3/1998 | Nicholson et al. | |
| 5,772,662 A | 6/1998 | Chapman et al. | |
| 5,871,485 A | 2/1999 | Rao et al. | |
| 5,899,938 A | 5/1999 | Sklar et al. | |
| 5,976,141 A | 11/1999 | Haag et al. | |
| 6,056,750 A | 5/2000 | Lob | |
| 6,290,701 B1 | 9/2001 | Enayati | |
| 6,355,044 B1 | 3/2002 | Hair | |
| 6,623,486 B1 | 9/2003 | Weaver et al. | |
| 2003/0065391 A1 | 4/2003 | Re et al. | |
| 2003/0074075 A1 | 4/2003 | Thomas, Jr. et al. | |
| 2003/0171753 A1* | 9/2003 | Collins et al. | 606/69 |
| 2003/0176863 A1 | 9/2003 | Ueyama et al. | |
| 2004/0162558 A1 | 8/2004 | Hegde et al. | |
| 2004/0176767 A1 | 9/2004 | Bickley | |
| 2006/0052787 A1 | 3/2006 | Re et al. | |
| 2006/0074421 A1 | 4/2006 | Bickley et al. | |
| 2006/0173455 A1 | 8/2006 | Matthys | |
| 2006/0184170 A1 | 8/2006 | Kapitan et al. | |
| 2008/0004626 A1 | 1/2008 | Glazer et al. | |
| 2008/0183220 A1 | 7/2008 | Glazer et al. | |

FOREIGN PATENT DOCUMENTS

| | | |
|---|---|---|
| DE | 89 08 858 | 12/1989 |
| DE | 4201531 | 7/1993 |
| DE | 298 23 395 | 9/1999 |
| EP | 0 089 298 A1 | 9/1983 |
| EP | 0 330 328 A1 | 8/1989 |
| EP | 0 596 829 A1 | 5/1994 |
| EP | 0 610 575 A3 | 8/1994 |
| EP | 1 018 321 A2 | 7/2000 |
| EP | 1 018 321 A3 | 4/2001 |
| GB | 89 08 858.1 | 1/1990 |
| GB | 2 266 246 A | 10/1993 |
| GB | 2 307 179 | 5/1997 |
| WO | WO-9848738 A1 | 5/1998 |
| WO | WO-9835635 A1 | 8/1998 |
| WO | WO-02/085182 A2 | 10/2002 |
| WO | WO-03/047440 A2 | 6/2003 |
| WO | WO-2004/006792 A1 | 1/2004 |

OTHER PUBLICATIONS

Regis W. Haid et al.; "The Cervical Spine Study Group anterior cervical plate nomenclature"; Neurosurg. Focus; Jan. 2002; pp. 1-6; vol. 12.

Scandius Biomedical; "TriTis Tibial Fixation System and Implant" Brochure from Scandius BioMedical, Inc. website http://www.scandius.com/documents/TriTisSSheetPlum3.pdf; Jan. 1, 2006.

PCT Search Report and Written Opinion of the ISA for PCT/US2006/000932 dated May 8, 2006.

Cook et al.; "Biomechanical Evaluation and Preliminary Clinical Experience with an Expansive Pedicle Screw Design;" Journal of Spinal Disorders; Jun. 13, 2000; pp. 230-236; vol. 13, No. 3.

Glatzmaier et al.; "Biodegradable Implants for Orthodontic Anchorage. A Preliminary Biomechanical Study;" European Journal of Orthodontics; 1996; pp. 465-469; vol. 18, No. 5.

Gualtieri et al.; "Biological and Mechanical Characteristics of the Interface Between a New Swelling Anchor and Bone;" Journal of Orthopaedic Research; pp. 494-499; vol. 18; The Journal of Bone and Joint Surgery, Inc.

McKoy et al.; "An Expandable Anchor for Fixation in Osteoporotic Bone;" Journal of Orthopaedic Research; Jun. 15, 1998, pp. 545-547; vol. 19.

Polly et al.; "Revision Pedicle Screws;" SPINE; 1998; pp. 1374-1379; vol. 23, No. 12; Lippincott-Raven Publishers.

Sklar; "Intrafix Technique for Tibial Fixation of ACL Grafts;" Innovasive Devices, Inc. P/N 900506, Rev. A; Aug. 2000; 5 Sheets.

PCT Search Report and Written Opinion of the ISA for PCT/US2004/014640 dated Nov. 14, 2004.

Patent Search Report; Smith & Nephew Corporate Patents & Trade Marks Department; Search No. S1951; Search Title Osteoporotic Screw System; Report No. 2002032; Search Period 1970 to Mar. 26, 2002; two sheets.

* cited by examiner

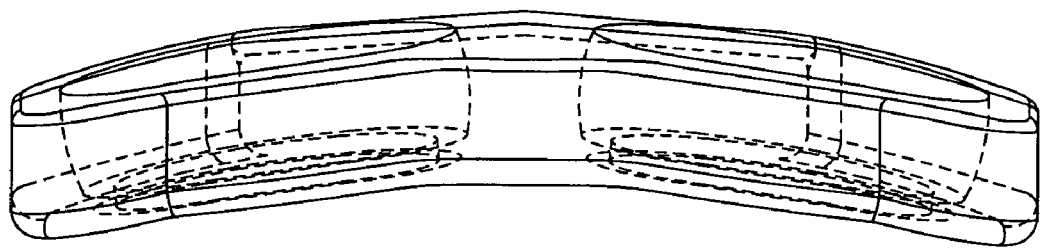
FIG. 24

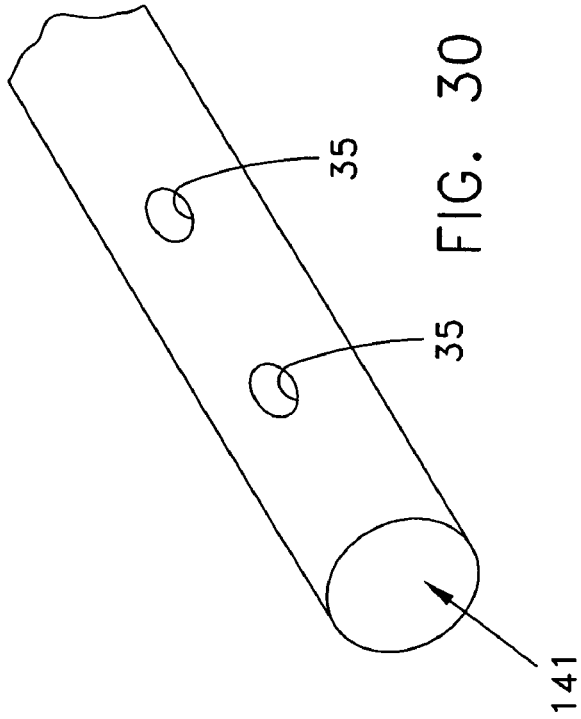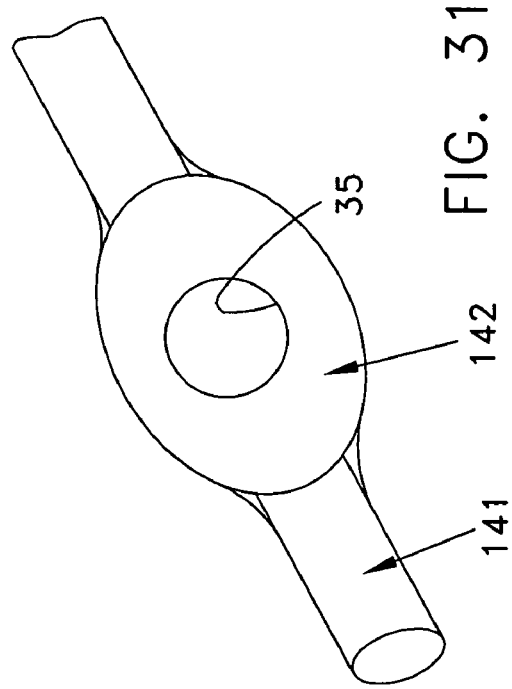

METHOD AND APPARATUS FOR SECURING AN OBJECT TO BONE

REFERENCE TO PENDING PRIOR PATENT APPLICATIONS

This patent application:

(1) is a continuation-in-part of pending prior U.S. patent application Ser. No. 10/554,379, filed Oct. 25, 2005 by Barry T. Bickley et al. for FIXATION AUGMENTATION DEVICE AND RELATED TECHNIQUES, which in turn claims benefit of:

(a) International (PCT) Patent Application No. PCT/US04/14640, filed May 10, 2004 for FIXATION AUGMENTATION DEVICE AND RELATED TECHNIQUES, which itself claims benefit of U.S. Provisional Patent Application Ser. No. 60/468,829, filed May 8, 2003 for FIXATION AUGMENTATION DEVICE; and (b) U.S. Non-Provisional patent application Ser. No. 10/246,304, filed Sep. 18, 2002 for FIXATION AUGMENTATION DEVICE AND RELATED TECHNIQUES; and (2) claims benefit of prior U.S. Provisional Patent Application Ser. No. 60/925,729, filed Apr. 23, 2007 by Barry T. Bickley et al. for METHOD AND APPARATUS FOR ATTACHING AN OBJECT TO BONE.

The five above-identified patent applications are hereby incorporated herein by reference.

FIELD OF THE INVENTION

This invention relates to surgical methods and apparatus in general, and more particularly to surgical methods and apparatus for securing an object to bone.

BACKGROUND OF THE INVENTION

In many situations an object may need to be secured to bone. By way of example but not limitation, where a bone is fractured, it may be desirable to stabilize the bone with a bone plate which extends across the fracture line. By way of further example but not limitation, where two separate bones need to be secured together (e.g., in the case of a spinal fusion), it may be desirable to secure the two bones to one another with a bone plate which extends from one bone to the other. By way of still further example but not limitation, where soft tissue needs to be attached (or re-attached) to bone (e.g., in the case of a ligament repair or reconstruction), it may be desirable to capture the soft tissue to the bone using a fixation plate.

In all of the foregoing situations, as well as many others which are well known to those skilled in the art, a plate or other object needs to be secured to bone. Such attachment is most commonly effected by using a surgical screw which passes through a hole in the plate (or other object) and into the bone.

When using a surgical screw to secure a plate to bone, the plate is first aligned with the bone. Then a hole is drilled into the bone, by passing a drill through a pre-existing hole in the plate and into the bone. Next, the bone hole may be tapped. Then the surgical screw is passed through the hole in the plate and into the hole in the bone, whereby to secure the plate to the bone.

One problem which can arise during the foregoing procedure is that the hole in the bone may become stripped as the screw is inserted into the bone. When this occurs, the screw can no longer obtain adequate purchase in the bone, thereby undermining plate fixation. A screw having inadequate purchase is sometimes referred to as a "spinner". Spinners can occur for many reasons, including (i) inadequate bone quality, (ii) over-tightening of the screw, (iii) an error when drilling the hole in the bone, (iv) an error when tapping the hole in the bone, etc. As noted above, spinners generally result in inadequate fixation.

SUMMARY OF THE INVENTION

The present invention is intended to address the foregoing deficiencies of the prior art, by providing a new and improved method and apparatus for securing an object to bone.

More particularly, the present invention provides a new and improved fixation system for securing an object to bone.

In one preferred form of the present invention, the new fixation system comprises a plate which is to be secured to bone, and a sleeve and a screw for securing the plate to the bone. The plate comprises an opening which extends through the plate. The plate is placed against the bone and then a drill is used to form a hole in the bone beneath the opening. A sleeve is passed through the opening and into the hole in the bone. The sleeve and plate are formed so that the sleeve (and the recipient bone hole) can be disposed at any one of a variety of angles relative to the plate. A screw is then passed through the sleeve, radially expanding the sleeve so that the sleeve is simultaneously secured to both the bone and the plate.

In one preferred form of the invention, there is provided a surgical system comprising:

an object to be secured to bone, the object comprising an opening extending therethrough; and a sleeve/screw construction for securing the object to bone, the sleeve/screw construction comprising:

a sleeve adapted for positioning through the opening in the object and into the bone, the sleeve comprising:

a shank having a distal end and a proximal end and an opening extending from the distal end to the proximal end, wherein the opening narrows toward the distal end of the shank, and further wherein the distal end of the shank is slit so as to form a plurality of radially-expandable segments; and an enlarged head formed at the proximal end of the shank, the enlarged head being formed so as to be radially-expandable;

the sleeve being sized so that when the sleeve is positioned through the opening in the object and into the bone, at least a portion of the radially-expandable segments extend into the bone beyond the cortical bone/cancellous bone interface; and a screw adapted for positioning through the opening in the sleeve, the screw being sized so as to (i) radially expand the distal end of the sleeve so that the sleeve is secured to the bone, and (ii) radially expand the enlarged head of the sleeve so that the sleeve is secured to the object, whereby to secure the object to the bone.

In another preferred form of the invention, there is provided a surgical system comprising:

an object to be secured to bone, the object comprising an opening extending therethrough; and a sleeve/expander construction for securing the object to bone, the sleeve/expander construction comprising:

a sleeve adapted for positioning through the opening in the object and into the bone, the sleeve comprising:

a shank having a distal end and a proximal end and an opening extending from the distal end to the proximal end, wherein the opening narrows toward the distal end of the shank, and further wherein the distal end of the shank is slit so as to form a plurality of radially-expandable segments; and an enlarged head formed at the proximal end of the shank, the enlarged head being formed so as to be radially-expandable; and an expander adapted for positioning through the opening in the sleeve, the expander being sized so as to (i) radially expand the distal end of the sleeve so that the sleeve is secured to the bone, and (ii) radially expand the enlarged head of the sleeve so that the sleeve is secured to the object, whereby to secure the object to the bone.

And in another preferred form of the invention, there is provided a method for securing an object to bone, the method comprising the steps of:

providing an object having an opening extending therethrough, and providing a sleeve/expander construction for securing the object to bone, the sleeve/expander construction comprising:

a sleeve adapted for positioning through the opening in the object and into the bone, the sleeve comprising:

a shank having a distal end and a proximal end and an opening extending from the distal end to the proximal end, wherein the opening narrows toward the distal end of the shank, and further wherein the distal end of the shank is slit so as to form a plurality of radially-expandable segments; and an enlarged head formed at the proximal end of the shank, the enlarged head being formed so as to be radially-expandable; and an expander adapted for positioning through the opening in the sleeve, the expander being sized so as to (i) radially expand the distal end of the sleeve so that the sleeve is secured to the bone, and (ii) radially expand the enlarged head of the sleeve so that the sleeve is secured to the object, whereby to secure the object to the bone;

positioning the object against the bone;

placing the sleeve through the opening in the object and into the bone; and positioning the screw in the sleeve so as to secure the sleeve to the bone and to the object, whereby to secure the object to the bone.

BRIEF DESCRIPTION OF THE DRAWINGS

These and other objects and features of the present invention will be more fully disclosed or rendered obvious by the following detailed description of the preferred embodiments of the invention, which is to be read in conjunction with the attached drawings wherein like numbers refer to like parts, and further wherein:

FIGS. 21-25 are schematic views showing another preferred form of the plate;

FIG. 30 is a schematic view showing a rod for use with the sleeve/screw construction of the present invention;

FIG. 31 is a schematic view showing another form of rod for use with the sleeve/screw construction of the present invention;

DETAILED DESCRIPTION OF THE PREFERRED EMBODIMENTS

Figure 1:
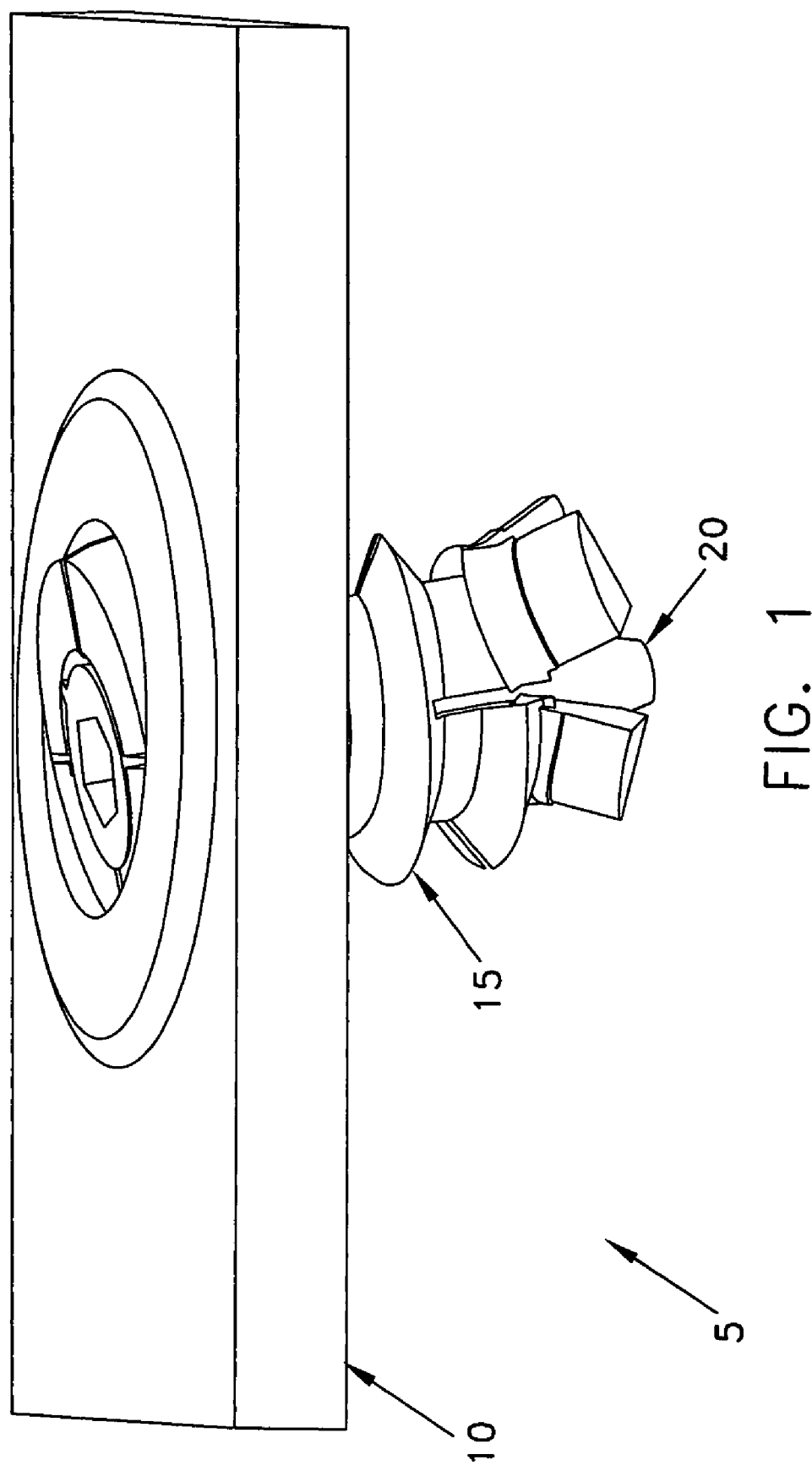
FIG. 1 is a schematic view showing one preferred form of the novel fixation system of the present invention.

Looking first at FIG. 1, there is shown a novel fixation system 5 which generally comprises a plate 10 which is to be secured to bone, and a sleeve 15 and a screw 20 for securing plate 10 to the bone.

Figure 2:
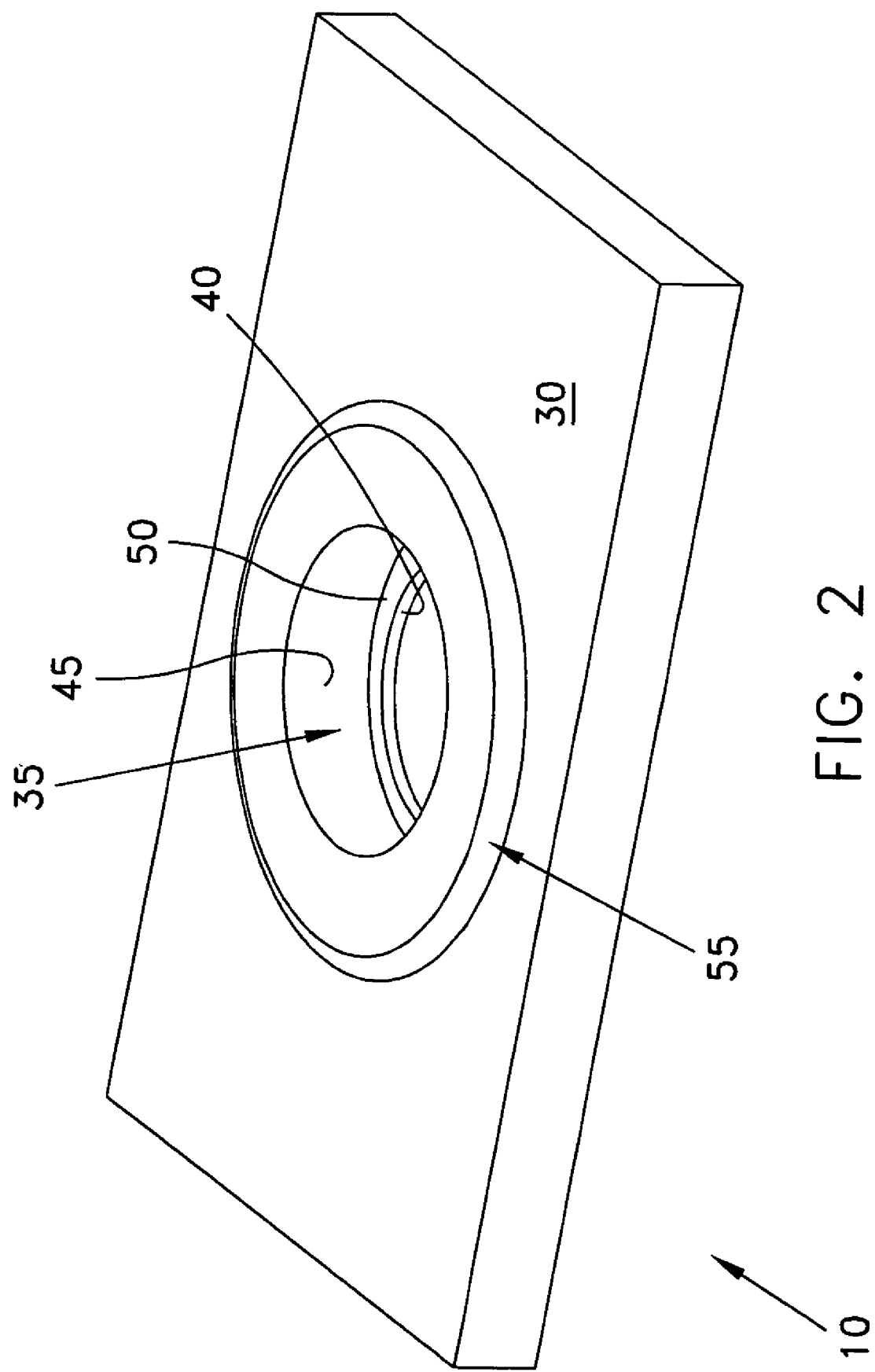
FIGS. 2 and 3 are schematic views showing one preferred form of the plate.
Figure 3:
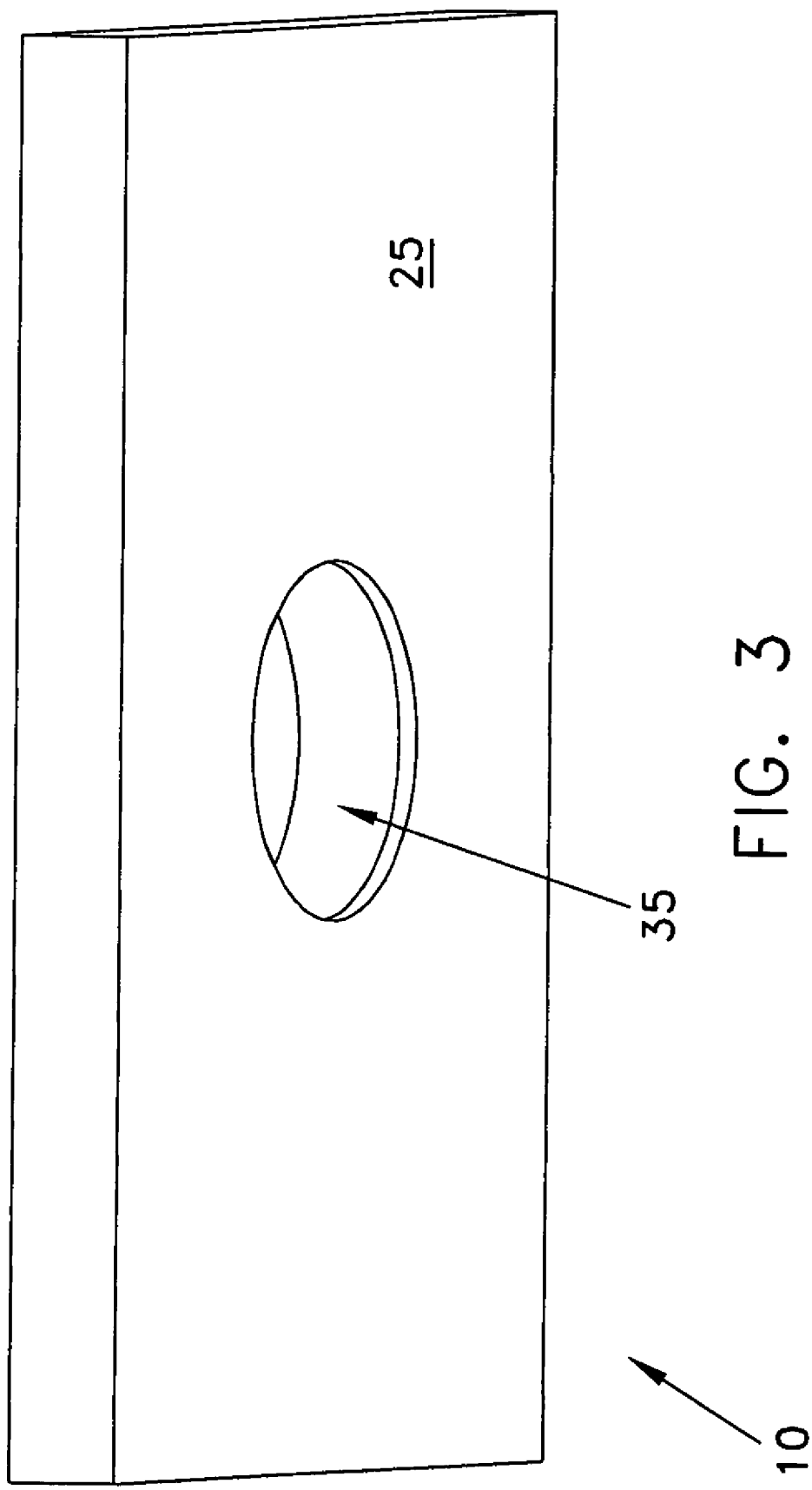

Plate 10 is shown in detail in FIGS. 2 and 3. Plate 10 generally comprises a distal surface 25 (FIG. 3) for positioning against bone, a proximal surface 30 (FIG. 2), and at least one opening 35 formed in the plate. Opening 35 is preferably in the form of a bore-counterbore configuration, i.e., a bore 40 opens on distal surface 25, a counterbore 45 opens on proximal surface 30, and an annular flange 50 is formed at the intersection of bore 40 and counterbore 45. As will hereinafter be discussed in further detail, bore 40 is sized to receive the shank of sleeve 15, and counterbore 45 is sized to receive the head of sleeve 15, with annular flange 50 serving to support the head of sleeve 15 and prevent the head of the sleeve from passing through the plate.

Opening 35 is preferably dimensioned, and one or more of the plate surfaces defining opening 35 are preferably appropriately radiused, and counterpart portions of sleeve 15 are preferably appropriately radiused, in order to permit sleeve 15 to extend through plate 10 at a range of different angles as will hereinafter be discussed in further detail. See, for example, FIG. 1, where sleeve 15 is shown extending through plate 10 at an acute angle.

A raised rim 55 is preferably formed on proximal surface 30 adjacent to opening 35. Raised rim 55 helps to present a smooth interface between the elements of the system and the surrounding tissue, particularly when sleeve 15 and screw 20 are placed at an acute angle relative to the plane of plate 10 (i.e., at an angle significantly off the perpendicular, such as is shown in FIG. 1). In addition, raised rim 55 also provides an enlarged contact surface for the head of sleeve 15, particularly when sleeve 15 and screw 20 are placed at an acute angle relative to the plane of plate 10 (i.e., an angle significantly off the perpendicular). See, for example, FIG. 1.

Depending on the intended use of plate 10, more than one opening 35 may be provided. By way of example but not limitation, where plate 10 is intended to be used as a fracture fixation plate or as a spinal fusion plate, at least one (and preferably two or more) openings 35 are formed in plate 10 on either side of the bone separation line (e.g., the fracture line, the vertebral body abutment lines, etc.), such that plate 10 can be secured to bone on each side of the bone separation line. By way of further example but not limitation, where plate 10 is intended to be used to secure soft tissue to bone, plate 10 might include only one opening 35.

Figure 4:
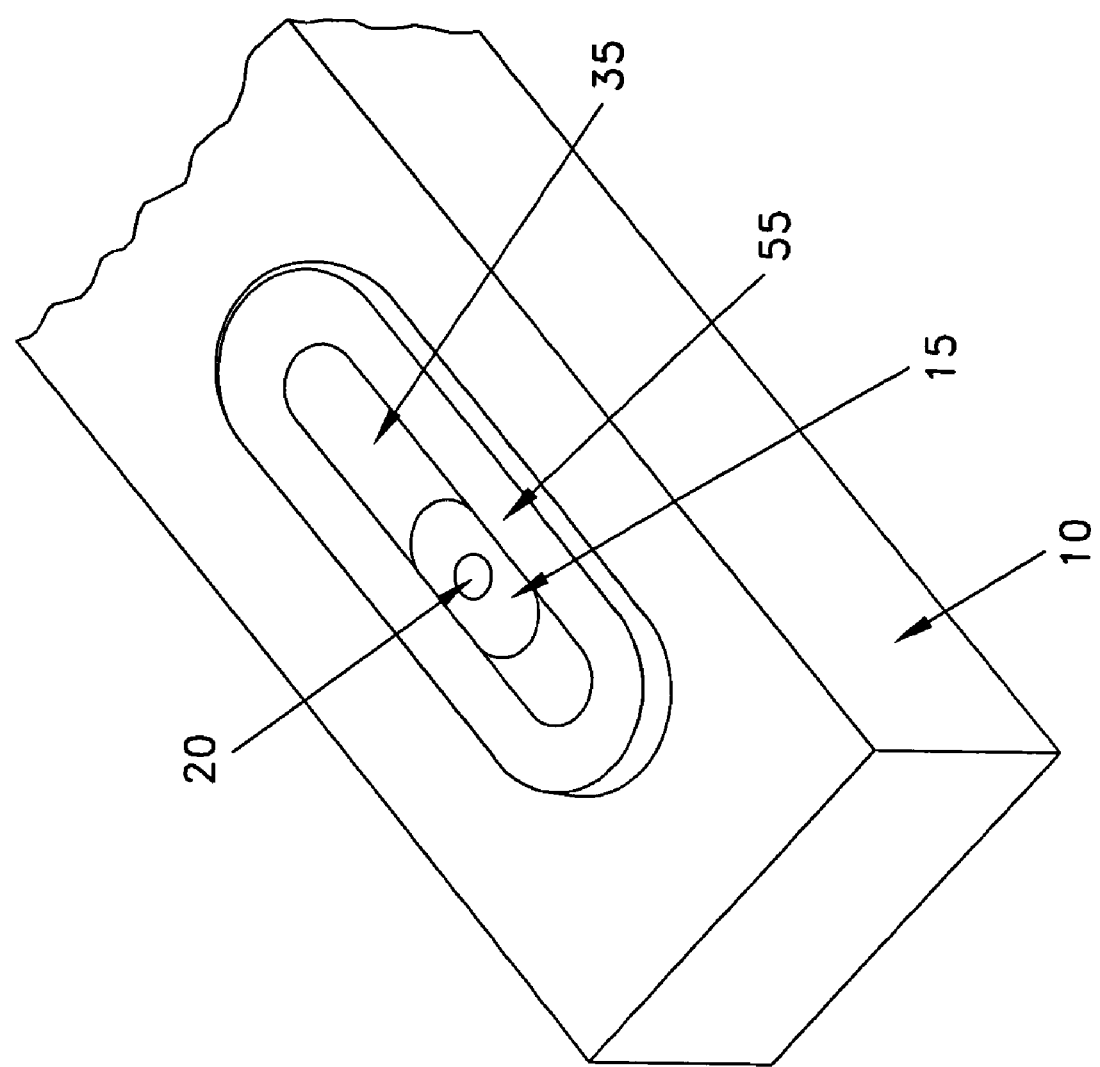
FIG. 4 is a schematic view showing an alternative form of plate and sleeve.
Figure 5:
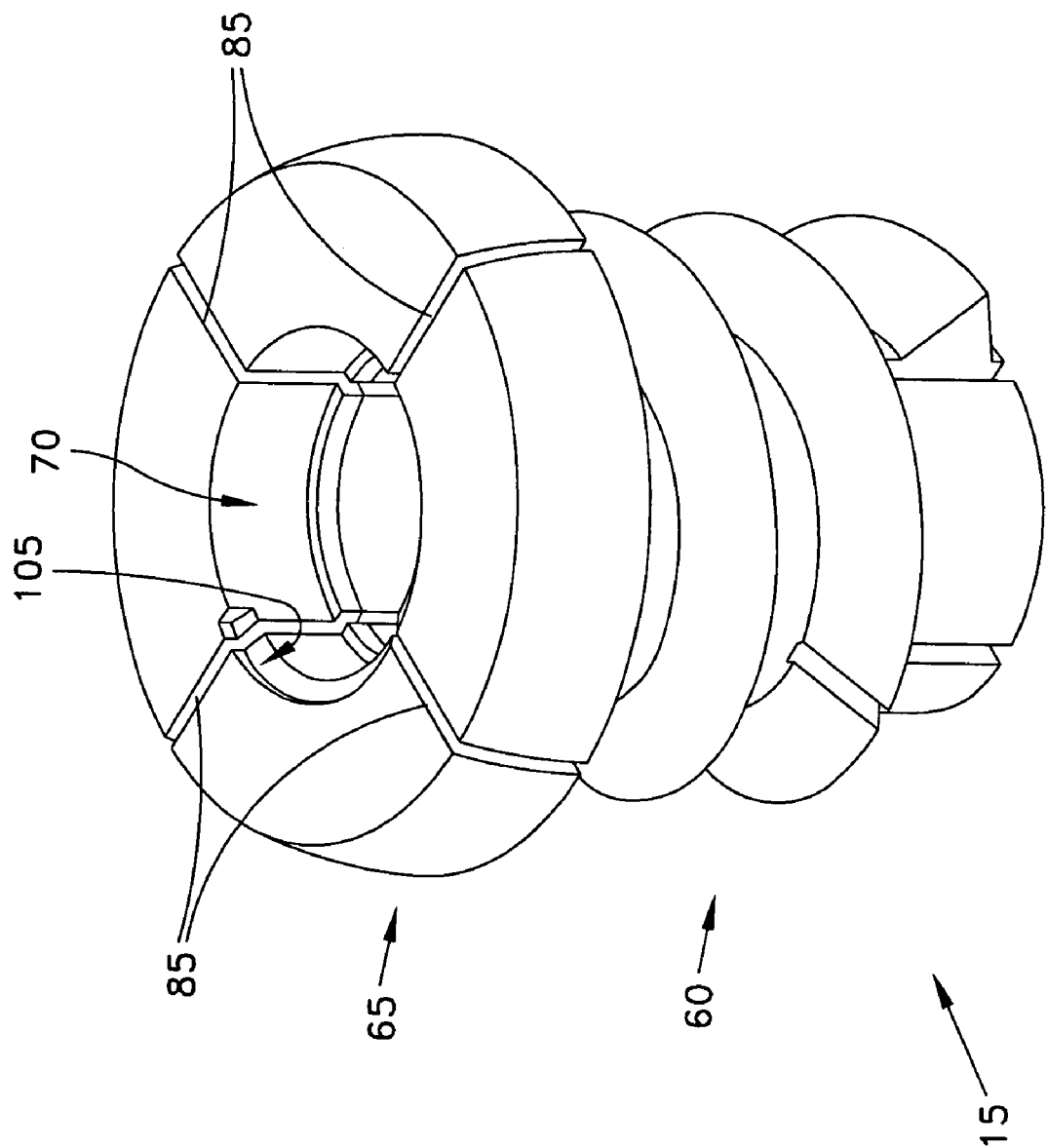
FIGS. 5-10 are schematic views showing one preferred form of the sleeve.
Figure 6:
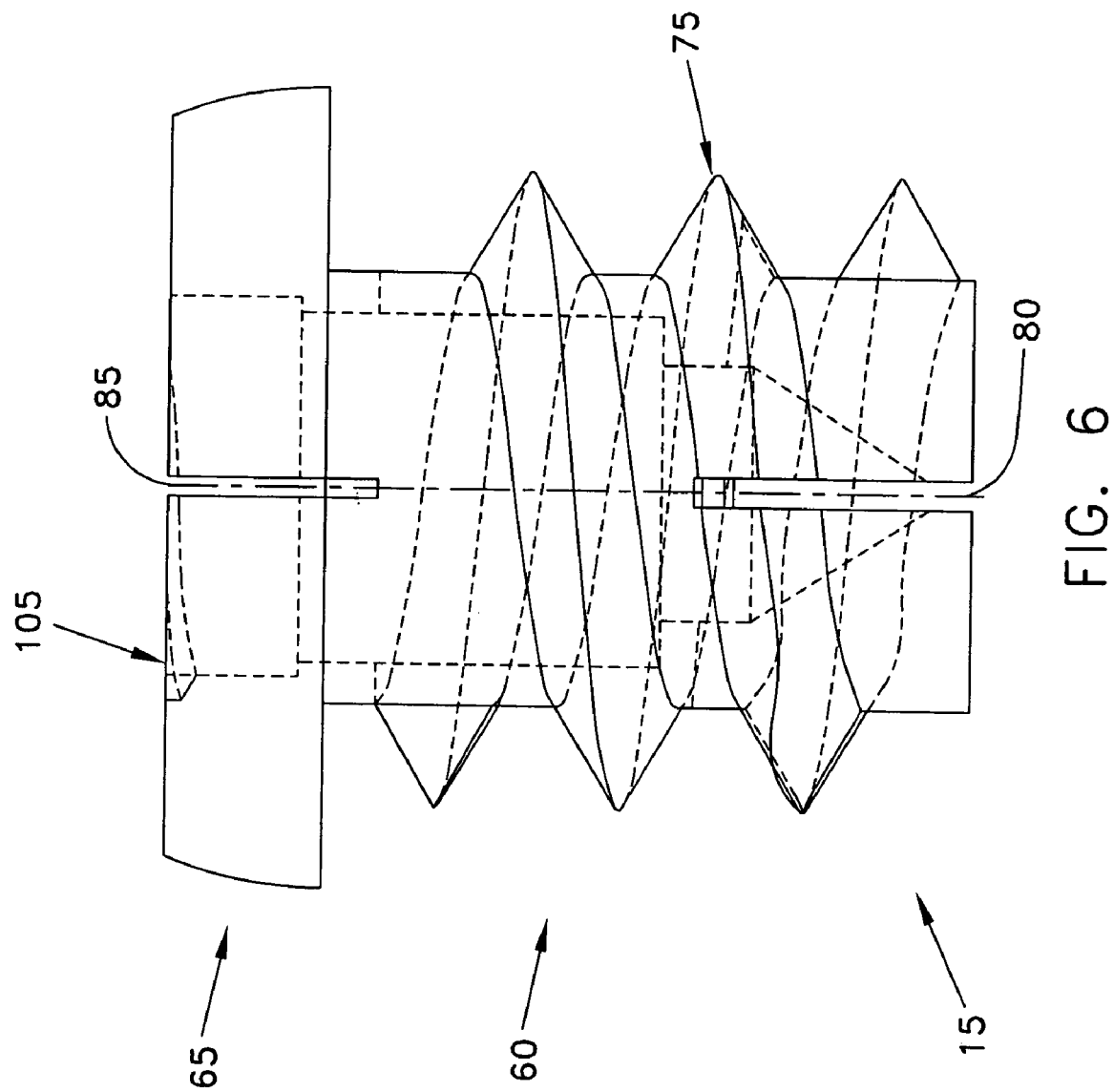
Figure 7:
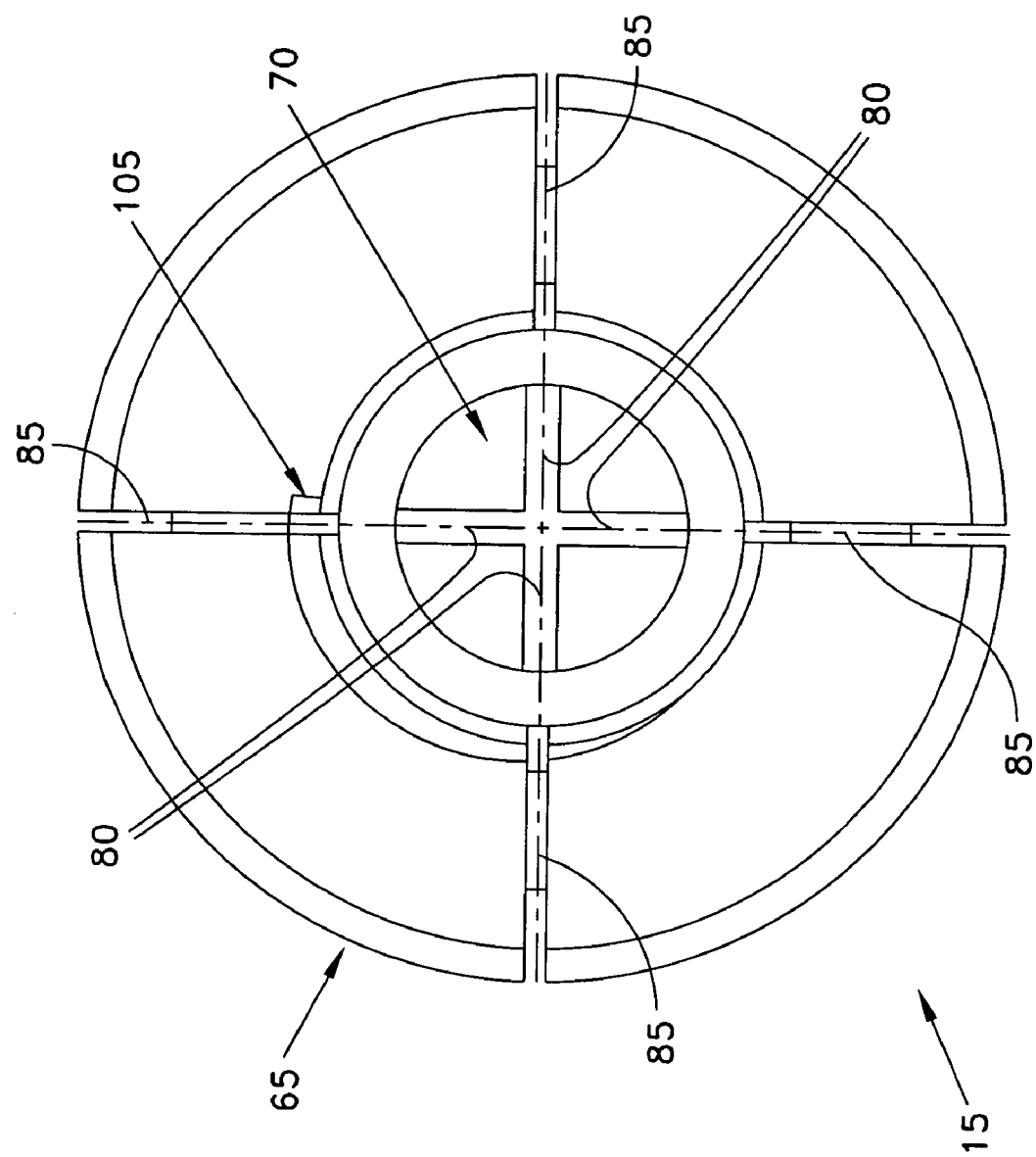
Figure 8:
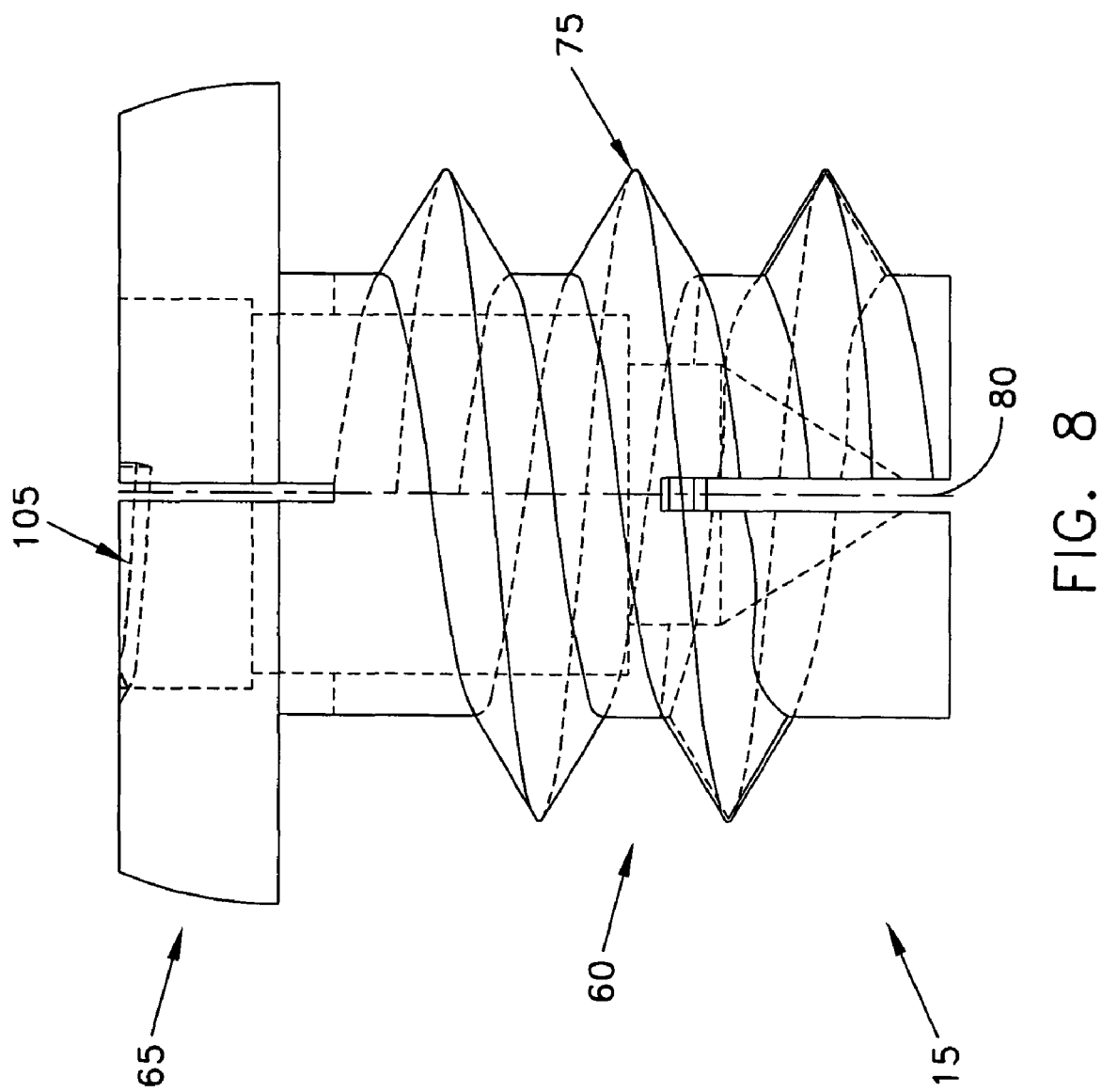
Figure 9:
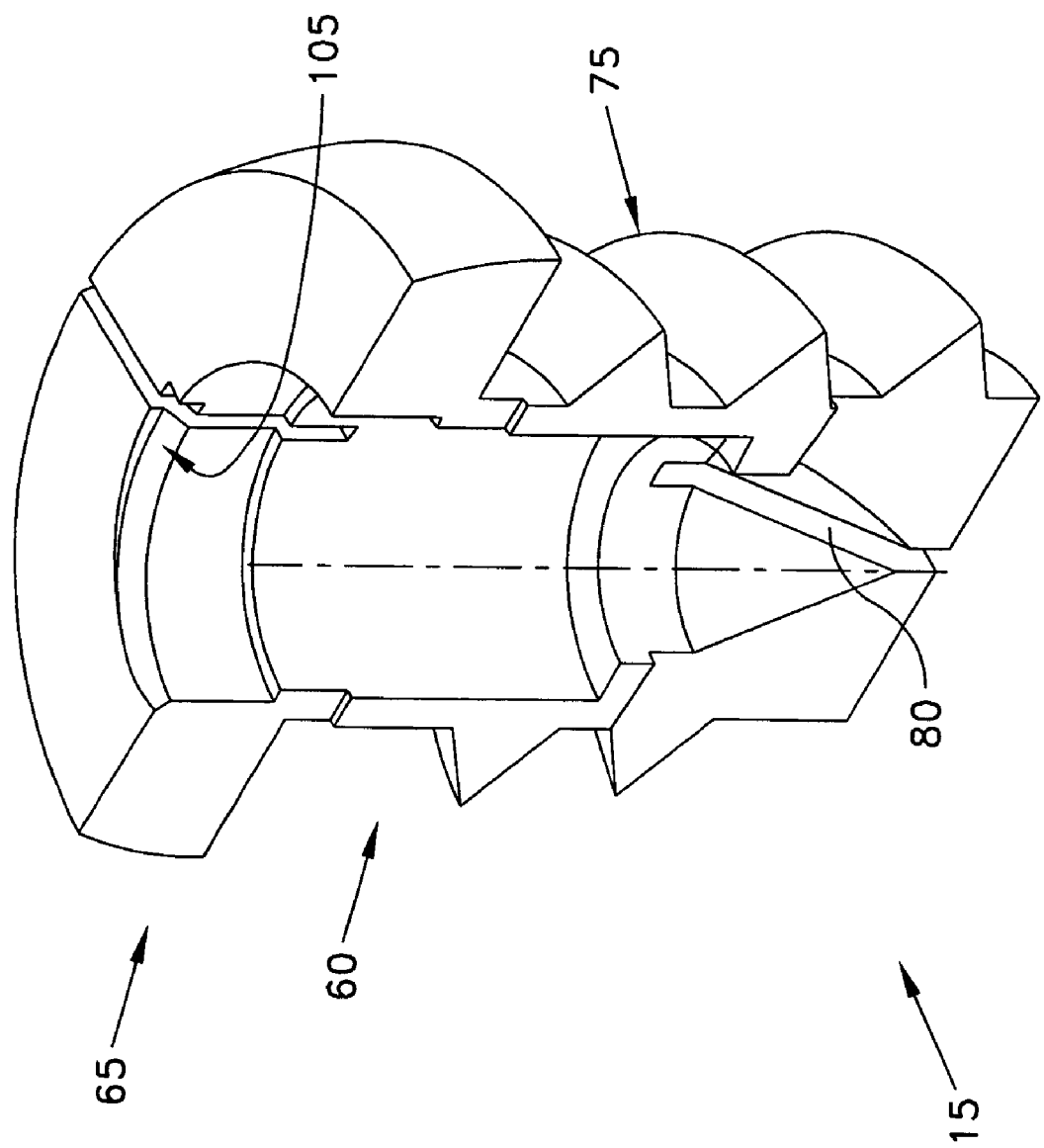
Figure 10:
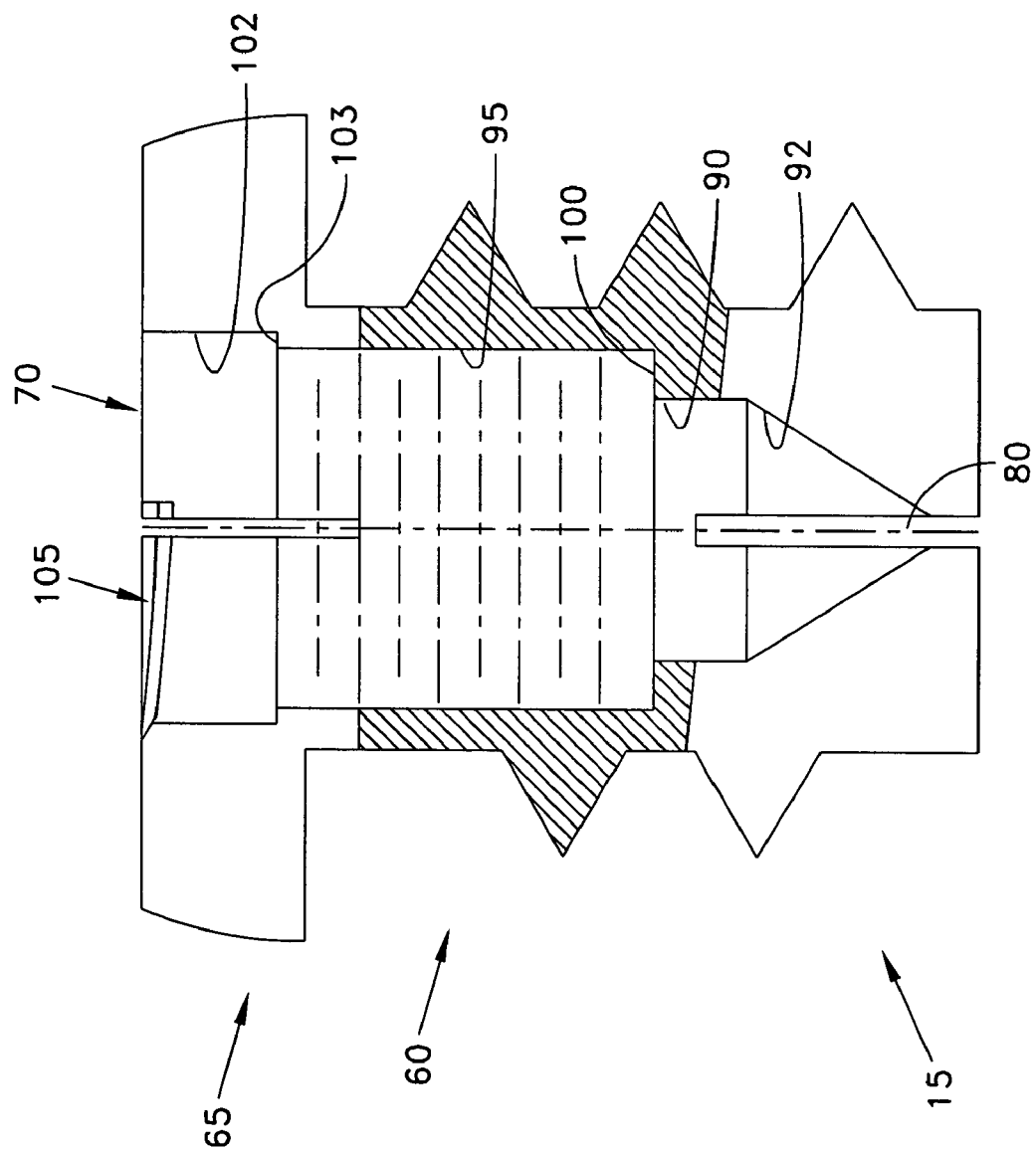
Figure 11:
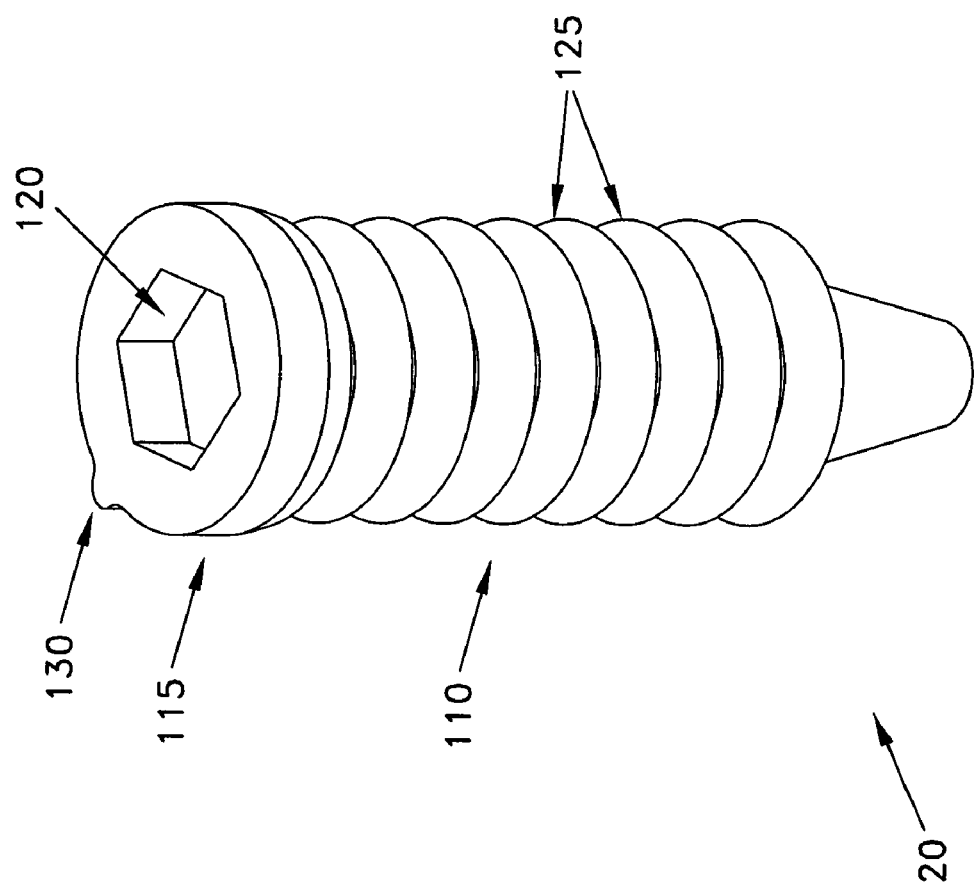
FIGS. 11-14 are schematic views showing one preferred form of the screw.
Figure 12:
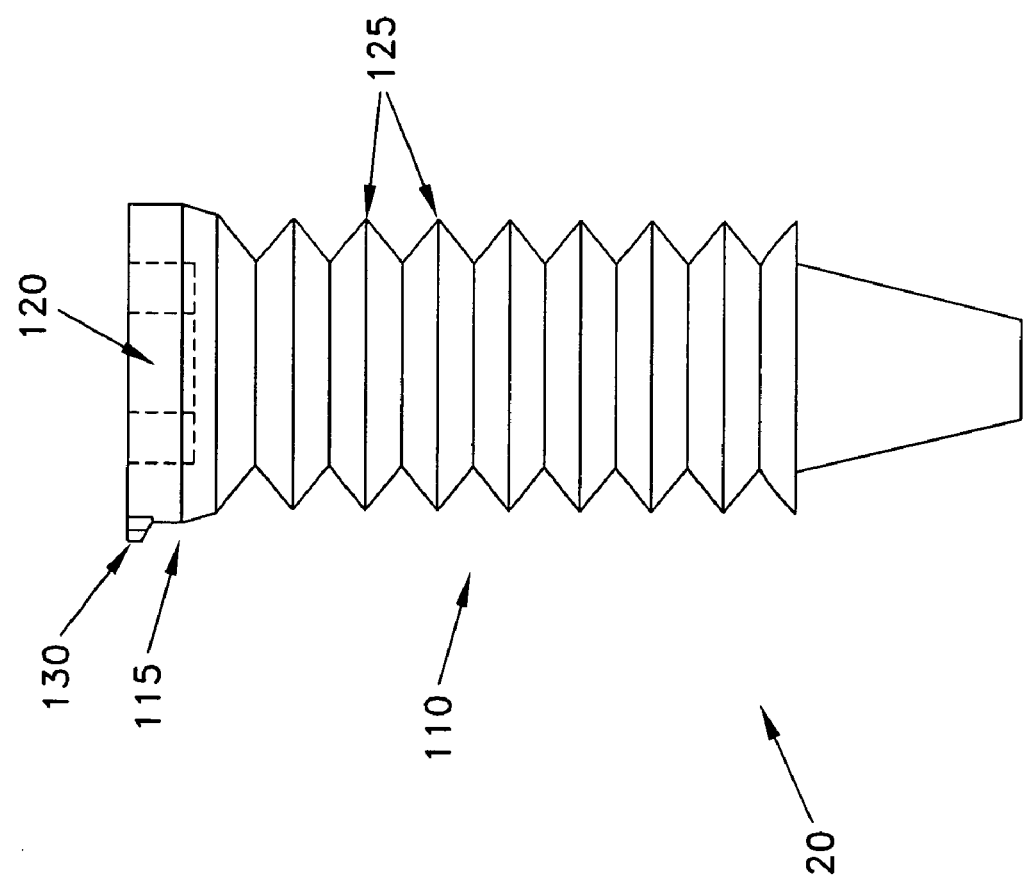
Figure 13:
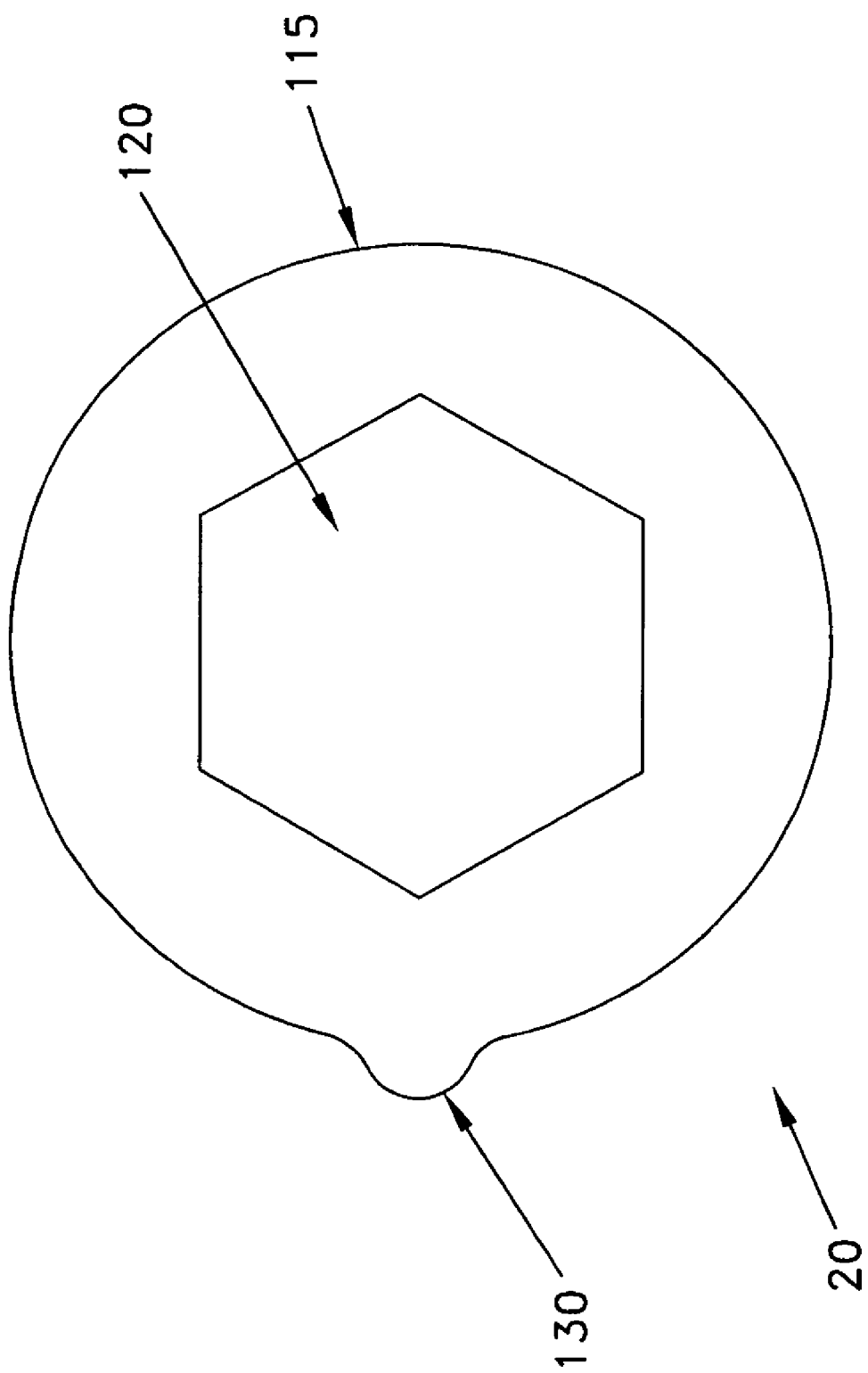
Figure 14:
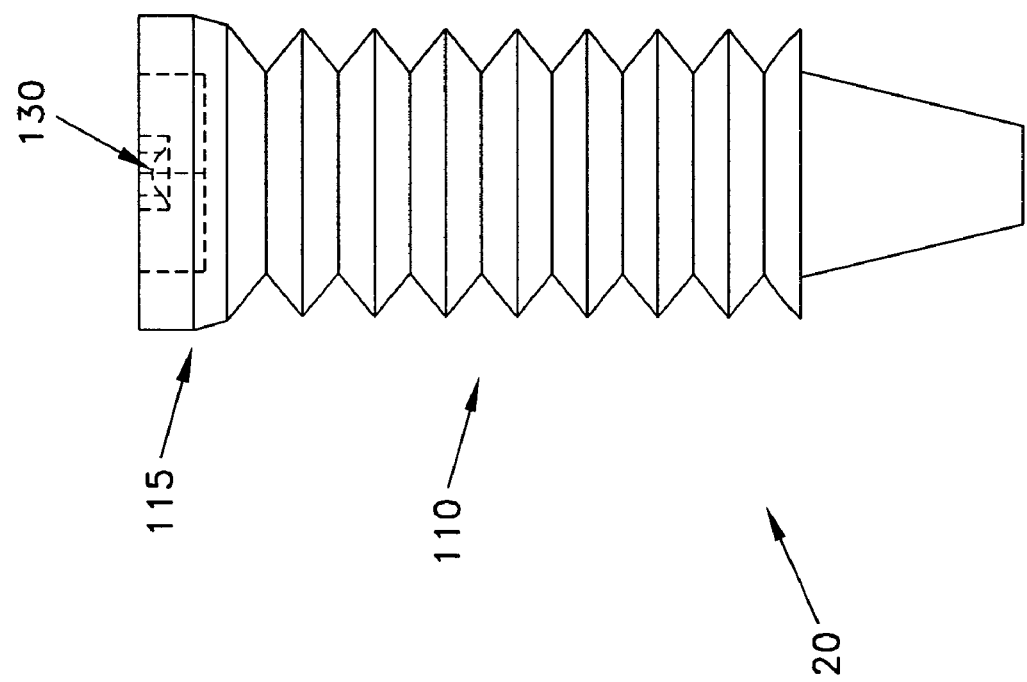

If desired, opening 35 in plate 10 and head 65 of sleeve 15 may be formed with non-circular (e.g., oval) shapes (as seen in top view) so as to provide an anti-rotation contact between the sleeve and the plate. Furthermore, if desired, opening 35 in plate 10 can have a slot-like configuration (as seen in top view), so as to allow a degree of longitudinal freedom when determining where to place sleeve 15 through opening 35 in plate 10. See FIG. 4.

Sleeve 15 is shown in detail in FIGS. 5-10. Sleeve 15 generally comprises a shank 60, a head 65 and an opening 70 extending along the length of sleeve 15.

Shank 60 comprises a screw thread 75 on its outer surface. Screw thread 75 is preferably configured to facilitate the gripping entry of sleeve 15 into bone when the sleeve is turned into bone. Such screw threads may be self-drilling, in which case it may not be necessary to pre-drill a hole in the bone. Furthermore, the threads may be self-tapping, or they may not be self-tapping, in which case it may be necessary to tap a bone hole before inserting the sleeve into that bone hole. Sleeve 15 may be formed with threads having a reverse face so as to aid in backing the sleeve out of the bone, in the event that the same should be desired (e.g., in the case of a revision).

A plurality of slits 80 extend through the side wall of shank 60 at the distal end of shank 60. Slits 80 permit shank 60 to expand radially when screw 20 is disposed in opening 70, as will hereinafter be discussed in further detail.

Head 65 includes a plurality of longitudinally-extending slots 85. Slots 85 permit sleeve 15 to be held against rotation as screw 20 is turned into the sleeve, as will hereinafter be discussed in further detail. Slots 85 also permit head 65 to expand when screw 20 is turned into the sleeve, whereby to facilitate head 65 gripping adjacent portions of plate 10, as will hereinafter be discussed in further detail. Additionally, the head of sleeve 15 can be formed with a beveled edge so that it stands less proud when the sleeve is inserted into plate 10 at an angle which is relatively far off the perpendicular.

Opening 70 comprises a bore-counterbore-counterbore configuration. More particularly, and looking now at FIG. 10, a bore 90, terminating in a tapered portion 92, communicates with distal slits 80. A counterbore 95 communicates with bore 90. An annular flange 100 is formed at the intersection of bore 90 and counterbore 95. Another counterbore 102 communicates with counterbore 95 and opens on the proximal end of sleeve 15. An annular shoulder 103 is formed at the intersection of counterbore 95 and counterbore 102. As will hereinafter be discussed, counterbore 95 is sized to receive the shank of screw 20, and counterbore 102 is sized to receive the head of screw 20, with annular shoulder 103 serving to support the head of screw 20. However, sleeve 15 and screw 20 are sized so that when screw 20 is received in opening 70 of sleeve 15, engagement of the shank of screw 20 with tapered portion 92 of sleeve 15 will radially expand the distal end of sleeve 15 so as to grip the bone. Furthermore, sleeve 15 and screw 20 are also sized so that when the head of screw 20 is seated in counterbore 102, screw 20 will radially expand head 65 of sleeve 15 so as to grip plate 10.

It should be appreciated that (i) the size and shape of the head of screw 20, (ii) the size and shape of counterbore 102, and (iii) the size and shape of slots 85 in the head of sleeve 15, can all be combined so as to "tune" the degree of expansion of head 65 of sleeve 15, whereby to regulate the force with which the sleeve is secured to plate 10.

In addition to the foregoing, and as will hereinafter be discussed in further detail, sleeve 15 is preferably sized so that, when sleeve 15 is deployed in a plate 10 and into a bone, the distal end of shank 60 will extend beyond the cortical bone/cancellous bone interface, so as to provide enhanced stabilization.

Thus, advancing screw 20 into sleeve 15 radially expands both the distal and proximal ends of sleeve 20, such that the sleeve is simultaneously secured to both the bone and the plate, as will hereinafter be discussed in further detail.

Bore 95 is preferably threaded so as to securely receive the shank of screw 20.

A radially-extending detent 105 is preferably formed in the side wall of counterbore 102, in order to receive a counterpart locking finger (see below) of screw 20, whereby to releasably lock screw 20 to sleeve 15, as will hereinafter be discussed in further detail.

Screw 20 is shown in detail in FIGS. 11-14. Screw 20 generally comprises a shank 110, a head 115 and an opening 120 extending longitudinally into screw 20. Shank 110 comprises a thread 125 on its outer surface. As noted above, head 115 includes a radially-extending locking finger 130 for seating in the radially-extending detent 105 formed in sleeve 15, whereby to releasably lock screw 20 to sleeve 15, as will hereinafter be discussed in further detail. Opening 120 has a non-circular cross-section (e.g., hexagonal), in order that screw 20 can be rotatably driven by an appropriate driver. Preferably screw 20 is sized so that when it is seated within sleeve 15, the distal end of the screw projects out of the distal end of the sleeve (see FIG. 1).

Sleeve 15 and screw 20 can be used to secure a plate to bone. By way of example but not limitation, sleeve 15 and screw 20 can be used to secure plate 10 to a fractured bone so as to stabilize that bone. In this circumstance, plate 10 extends across the fracture line, with each end of the plate being secured to the bone using a sleeve/screw construction. Significantly, each sleeve/screw construction can be oriented at a different angle relative to plate 10, so as to better distribute load and/or apply a compressive force.

Figure 15:
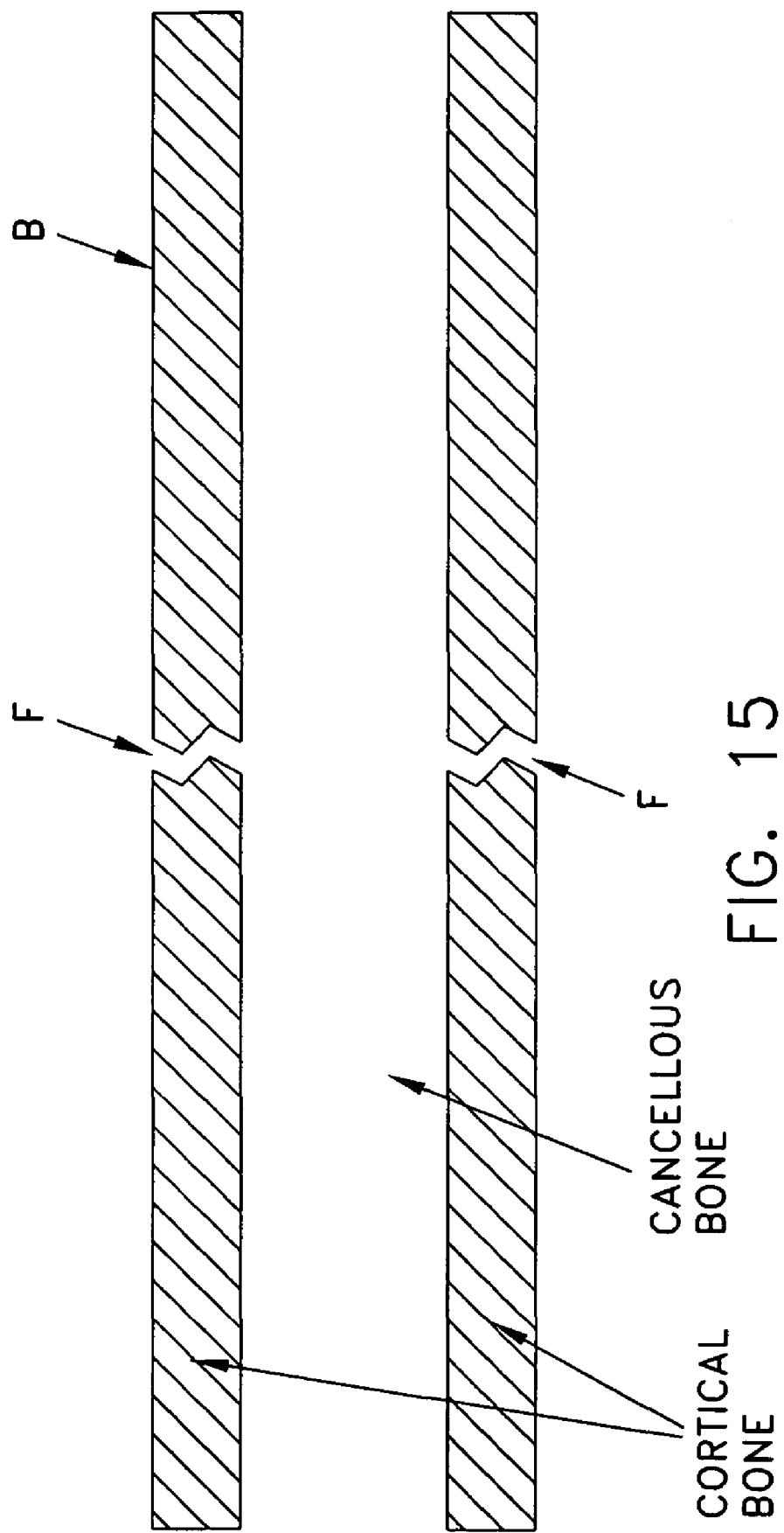
FIGS. 15-20 are schematic views showing the plate being secured to a bone using a plurality of sleeve/screw constructions.
Figure 16:
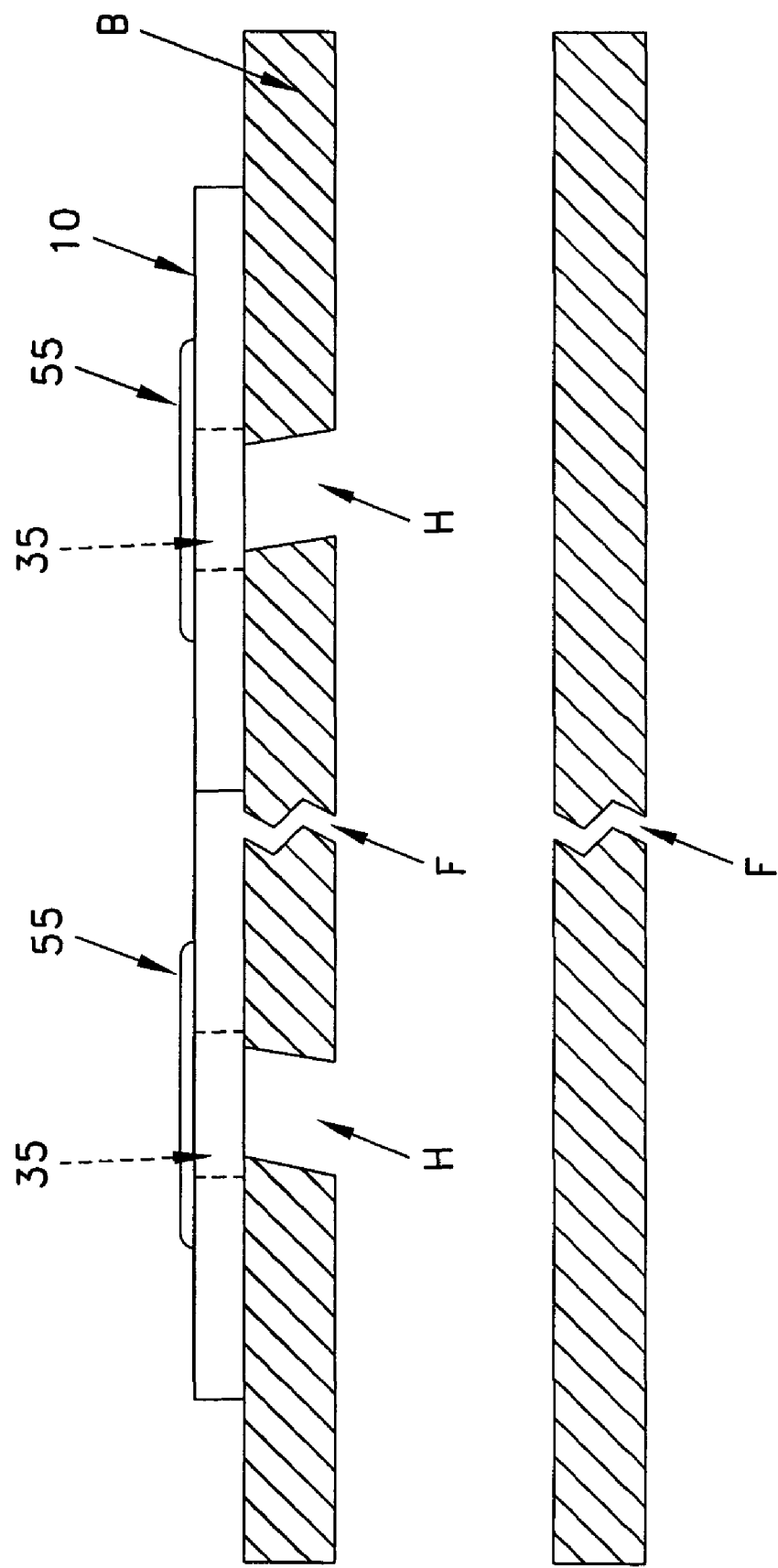

More particularly, and looking now at FIG. 15, there is shown a bone B having a fracture F. In order to stabilize fracture F, a plate may be secured to the bone on either side of fracture F. To this end, and looking now at FIG. 16, plate 10 is positioned against bone B, and then a hole H is drilled into the bone beneath of the openings 35 which is to receive a sleeve/screw construction. This is done by passing a drill through opening 35 in plate 10 and into the bone. Due to the construction of plate 10 and sleeve 15, bone hole H can be set at any one of a number of different orientations relative to plate 10, e.g., bone hole H can extend at an acute angle relative to the plane of plate 10 (see, for example, FIG. 16) or bone hole H can extend at a right angle to the plane of plate 10 (not shown). This construction allows the surgeon to select the most desirable orientation for the bone hole, taking into account factors such as bone quality, force distribution, angle of approach, etc.

Figure 17:
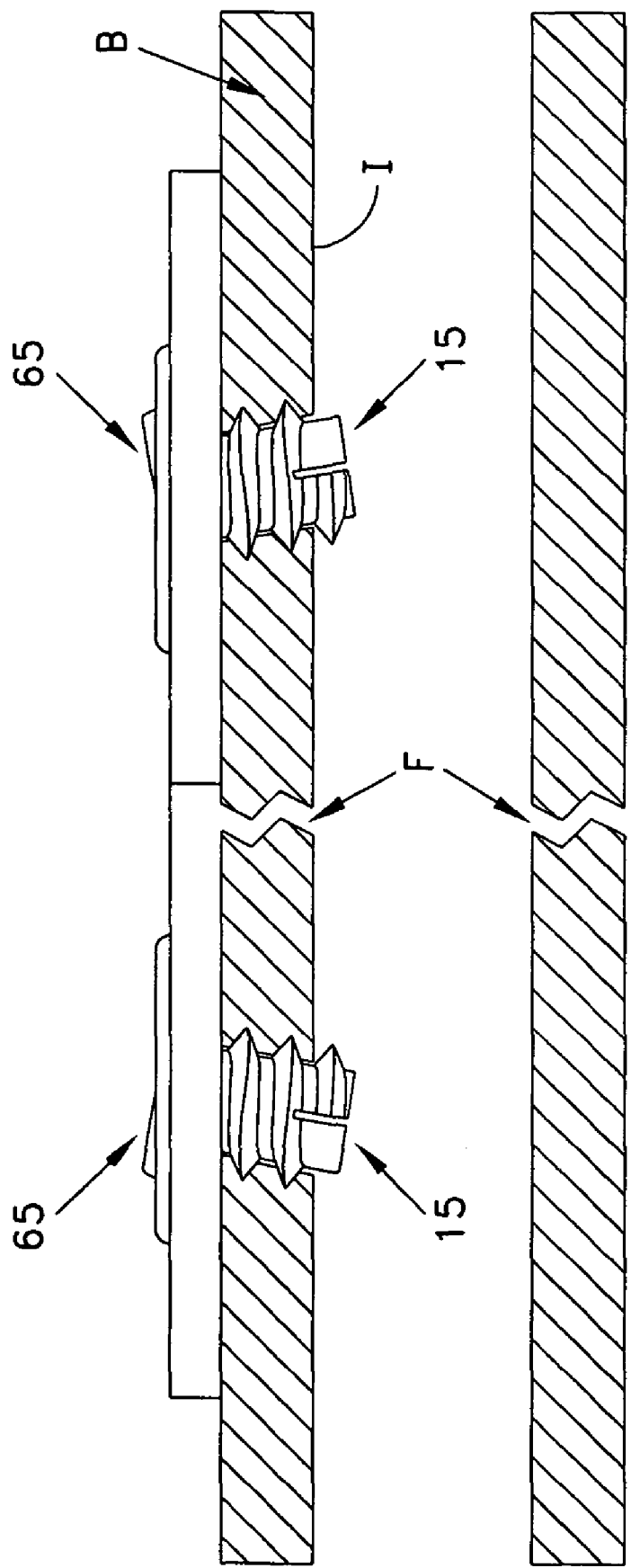
Figure 18:
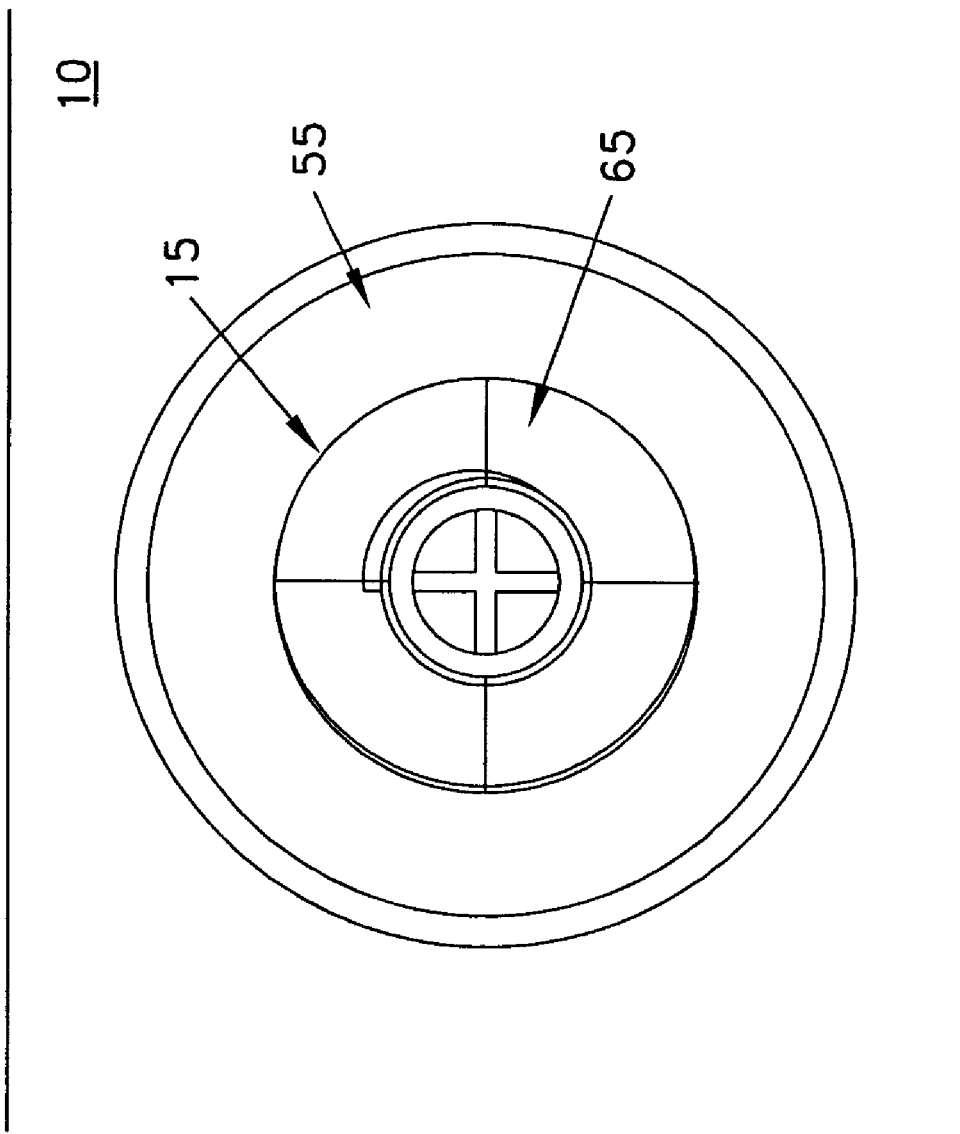

Once bone holes H have been drilled in bone B, sleeves 15 are advanced through plate openings 35 and into bone holes H (FIGS. 17 and 18). This is done by turning sleeve 15 with an appropriate rotational driver. Sleeve 15 is advanced until shank 60 is disposed in bone B and head 65 is seated in plate counterbore 45. At this point, sleeve 15 will serve to provide some degree of attachment of plate 10 to bone B, by virtue of the engagement of screw threads 75 with bone B and head 65 with counterbore 45.

As noted above, sleeve 15 is preferably sized so that, when sleeve 15 is deployed in a plate 10 and into bone B (FIG. 17), the distal end of shank 60 extends beyond the cortical bone/cancellous bone interface I, so as to provide enhanced stabilization, as will hereinafter be discussed in further detail.

Figure 19:
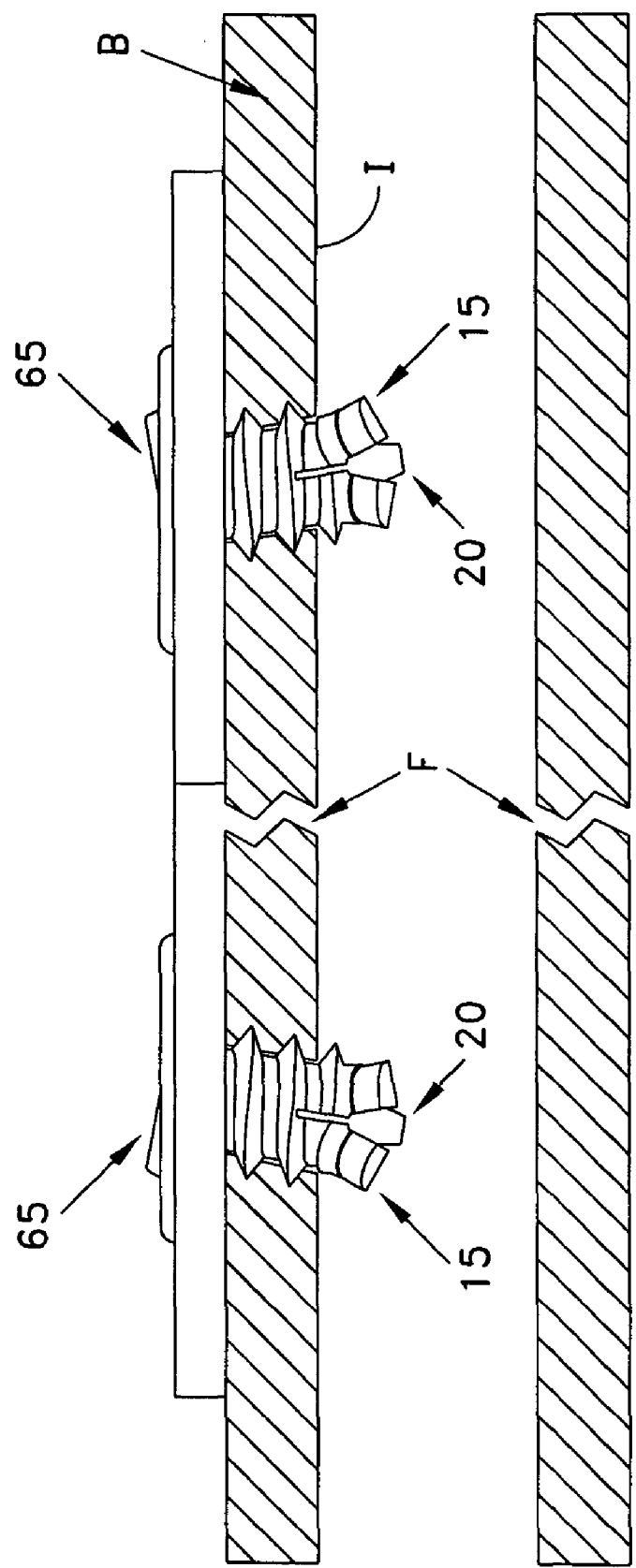
Figure 20:
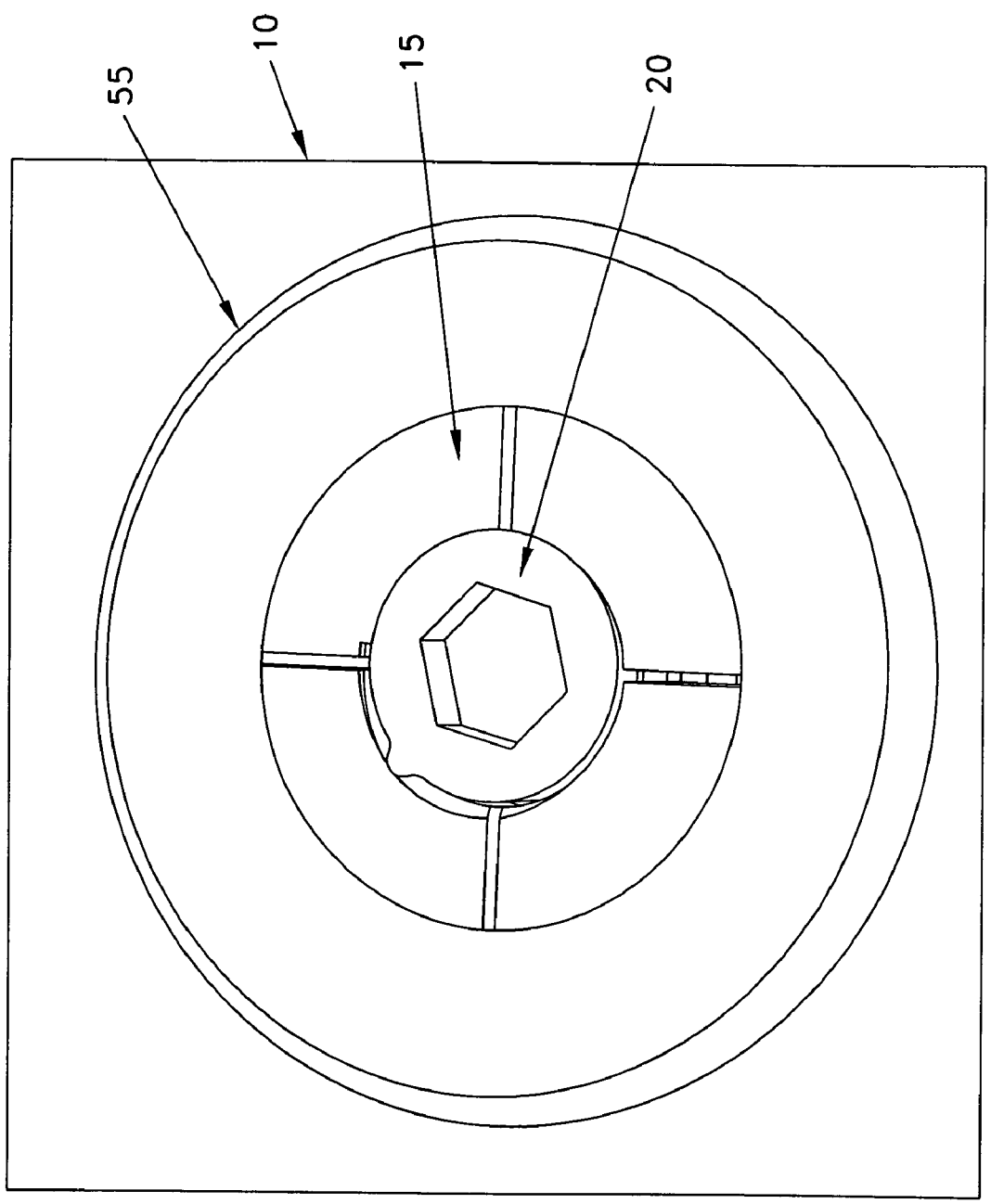
Figure 21:
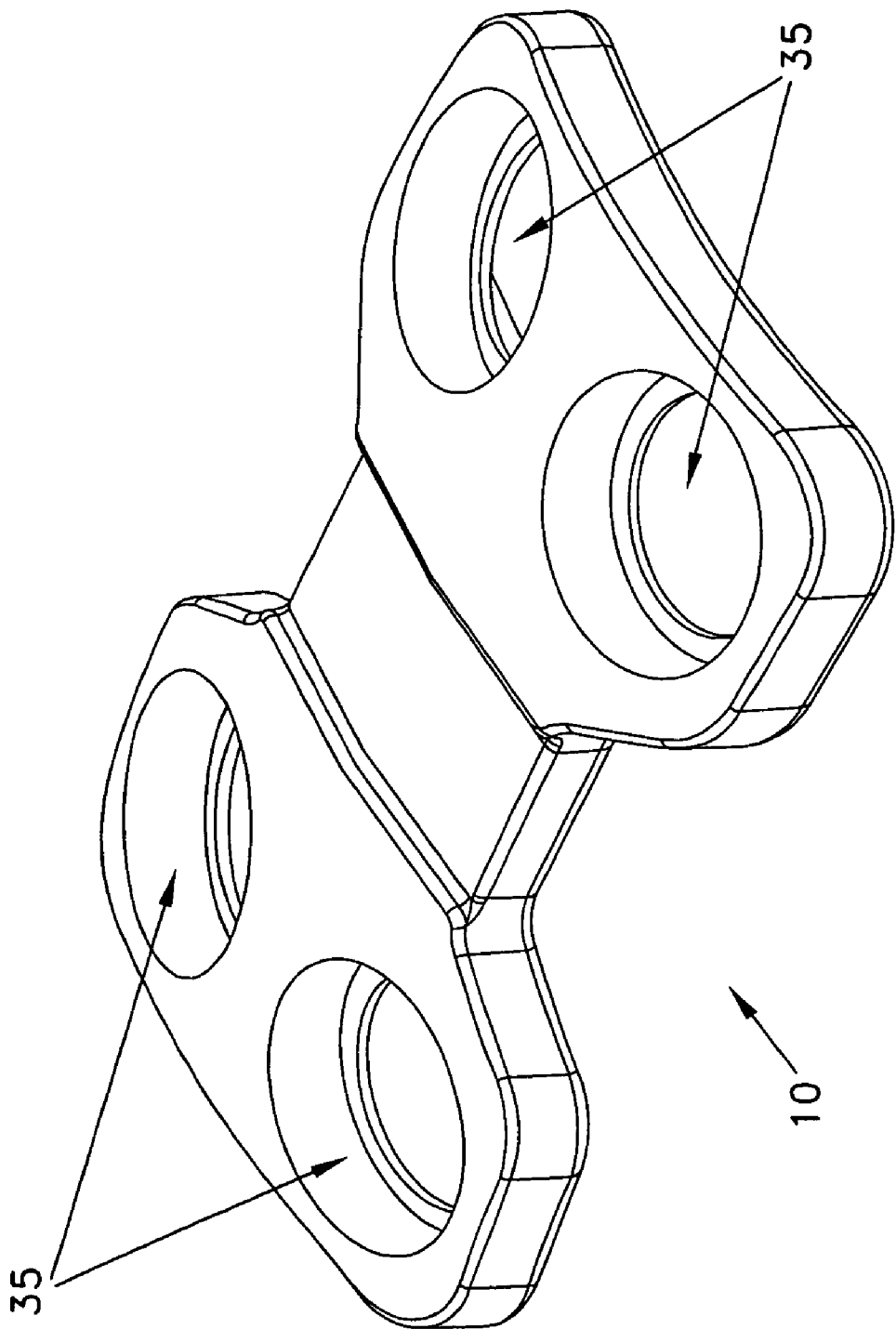
Figure 22:
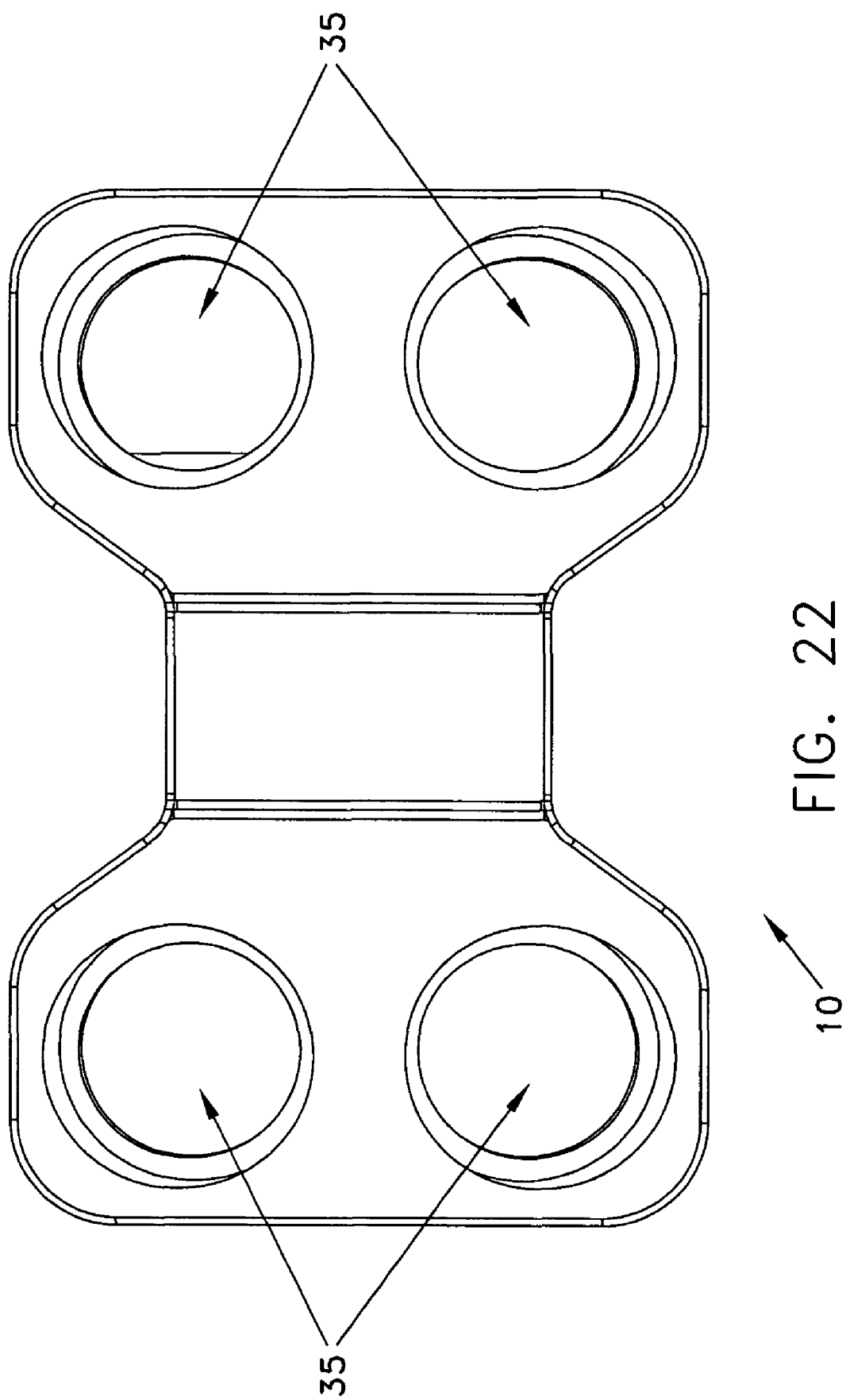
Figure 23:
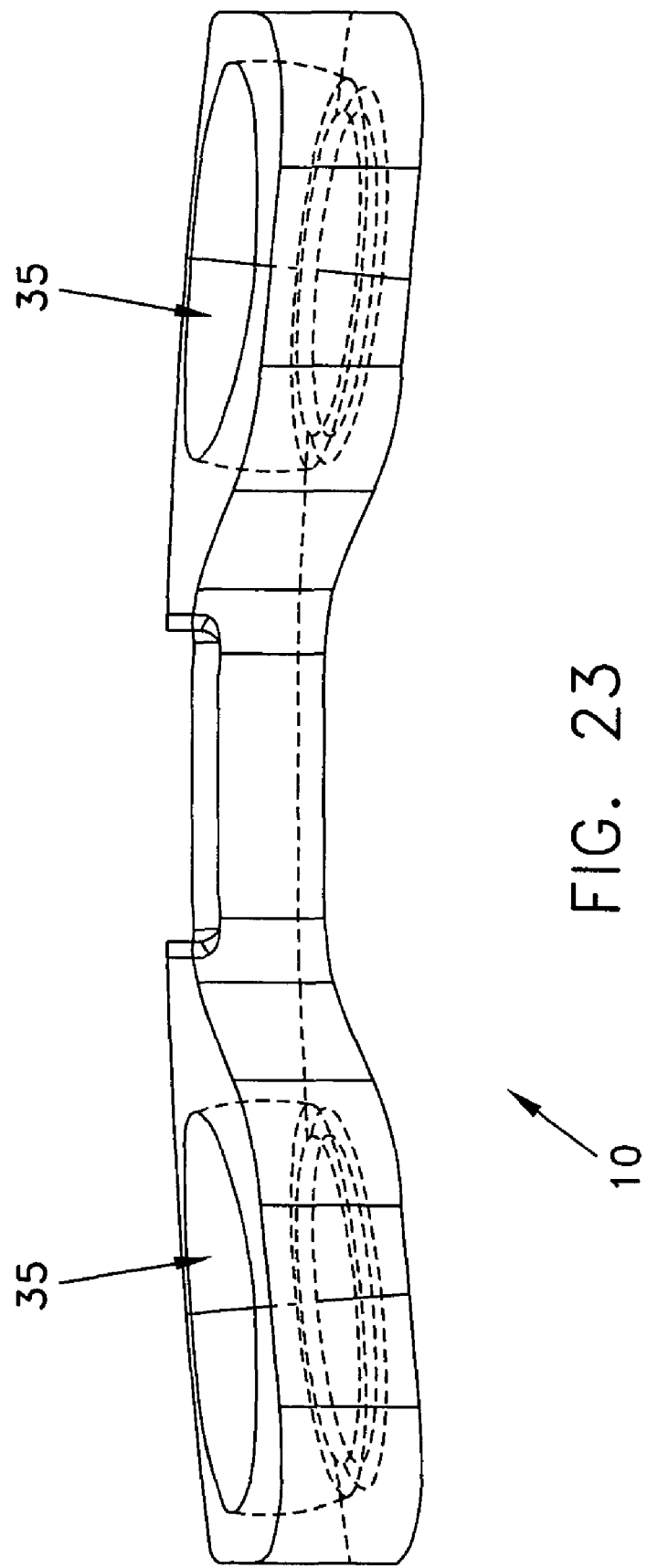
Figure 25:
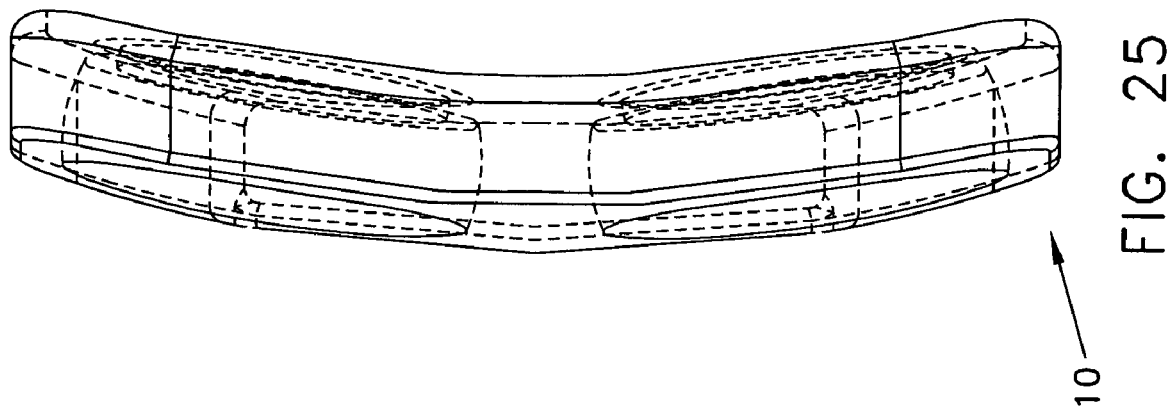

Next, screw 20 is advanced down opening 70 in sleeve 15 (FIGS. 19 and 20). As this occurs, sleeve 15 can be held against rotation using sleeve slots 85. The advancing screw 20 causes sleeve 15 to be radially expanded, so that the sleeve is simultaneously secured to both bone B and to plate 10. More particularly, the distal end of the sleeve's shank 60 is expanded so that the sleeve engages the cancellous portion of bone B, the proximal end of the sleeve's shank 60 engages the cortical portion of bone B, and the sleeve's head 65 engages plate 10. Significantly, sleeve 15 is sized so that the distal end of the sleeve mushrooms open beyond the cancellous bone/cortical bone interface I, making a tight securement between plate 10 and bone B.

Screw 20 is advanced until locking finger 130 seats in sleeve detent 105, thereby releasably locking the screw in position relative to the sleeve. Engagement of locking finger 130 in sleeve detent 105 also serves as an indicator, with tactile feedback, that the screw has been advanced to the proper extent (and not overtightened) relative to the sleeve.

Significantly, inasmuch as sleeve 15 opens laterally and presents a substantially larger profile than screw 20 alone, the disposition of the combination of sleeve and screw in the plate and the bone provides much better contact with the plate and the bone, thereby enhancing securement and shear resistance. This is particularly true since the distal end of sleeve 15 opens just beyond the cortical bone/cancellous bone interface I, so that plate 10 is secured to bone B under tension. In addition, since screw 20 is being advanced into sleeve 15 and not directly into the bone, there is little likelihood that the screw will lose its purchase and become a spinner. Furthermore, in the unlikely event that the screw should become a spinner, the situation can be easily rectified by removing screw 20 from sleeve 15 and removing sleeve 15 from the bone and plate 10. This leaves the host bone in condition for the procedure to be repeated with a new sleeve and/or a new screw, reusing the same bone hole.

Additional Constructions

It is possible to modify the constructions described above without departing from the scope of the present invention.

By way of example but not limitation, plate 10 might be formed with a non-rectangular and/or curved configuration, so as to seat more securely against a curved bone surface. See, for example, FIGS. 21-25, which show one such construction for plate 10.

Figure 26:
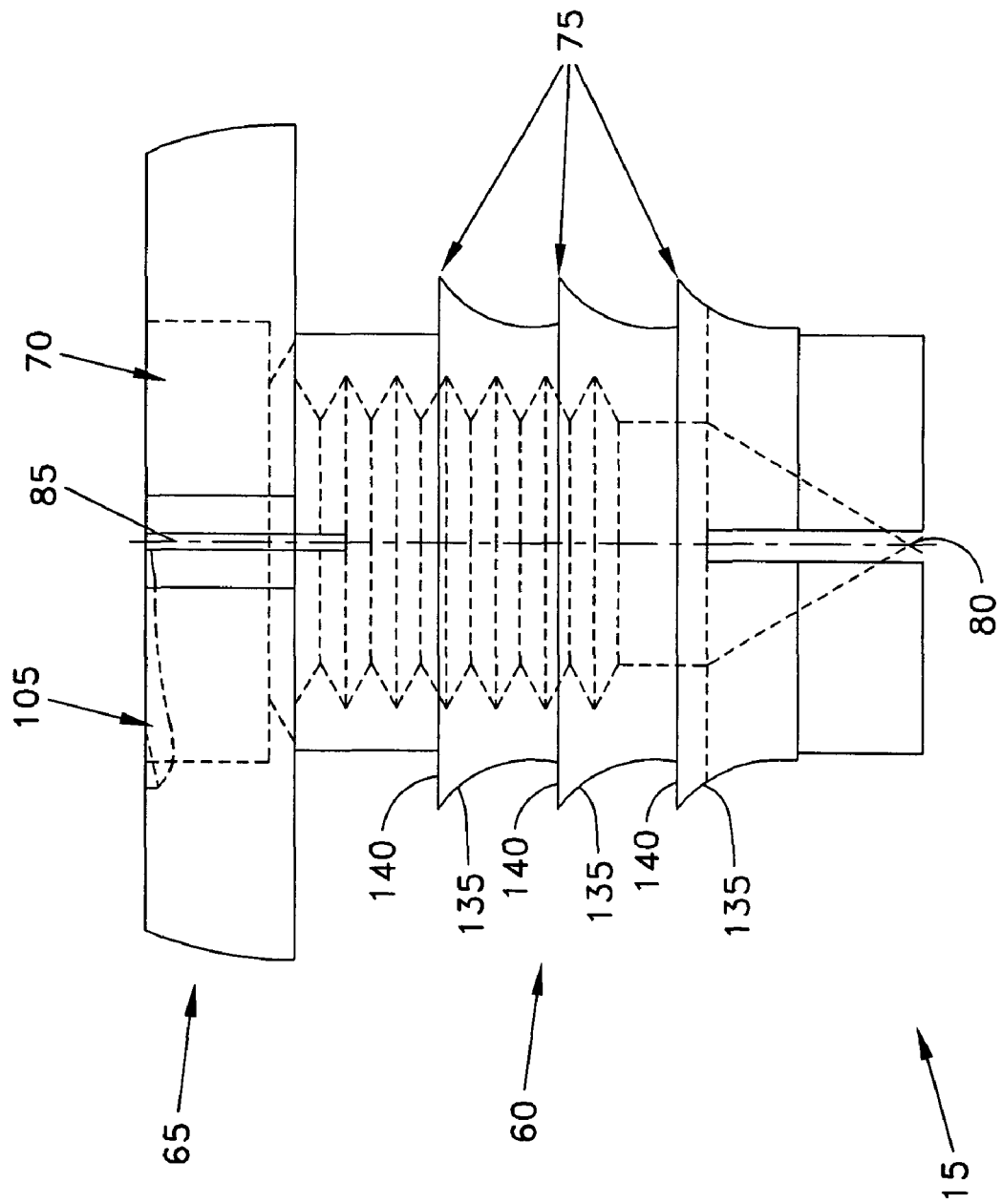
FIGS. 26-28 are schematic views showing another preferred form of the sleeve.
Figure 27:
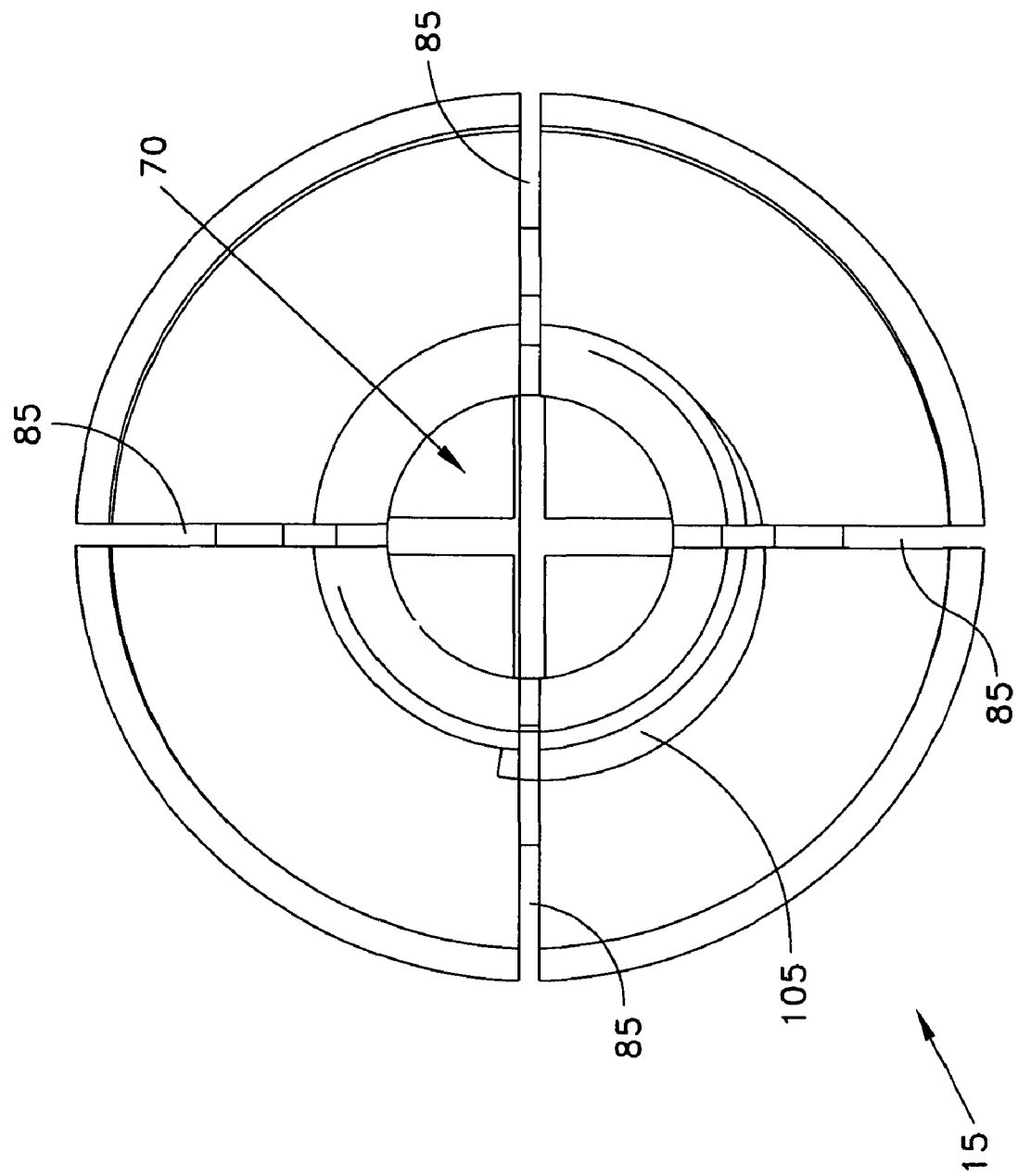
Figure 28:
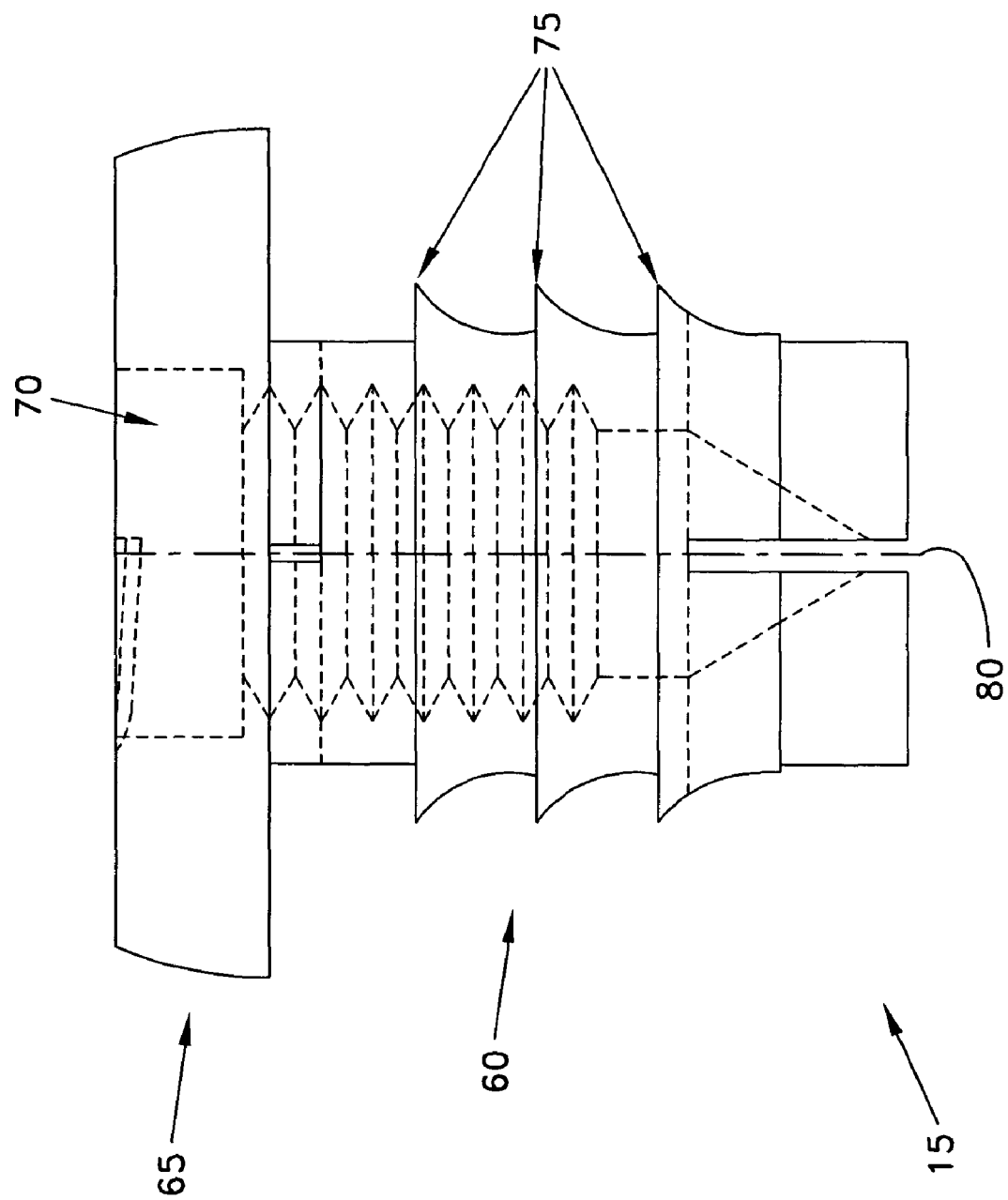

By way of further example but not limitation, sleeve 15 might be formed with ribs (or other lateral projections) 75 instead of a screw thread 75. See, for example, FIGS. 26-28, which show a sleeve 15 formed with ribs 75. In this case, sleeve 15 might be set with a mallet driver, etc., rather than with a rotational driver. Where sleeve 15 is formed with ribs 75, ribs 75 may be given a profile to facilitate insertion and impede withdrawal from the bone, e.g., sloped leading edges 135 and sharp rims 140.

Figure 29:
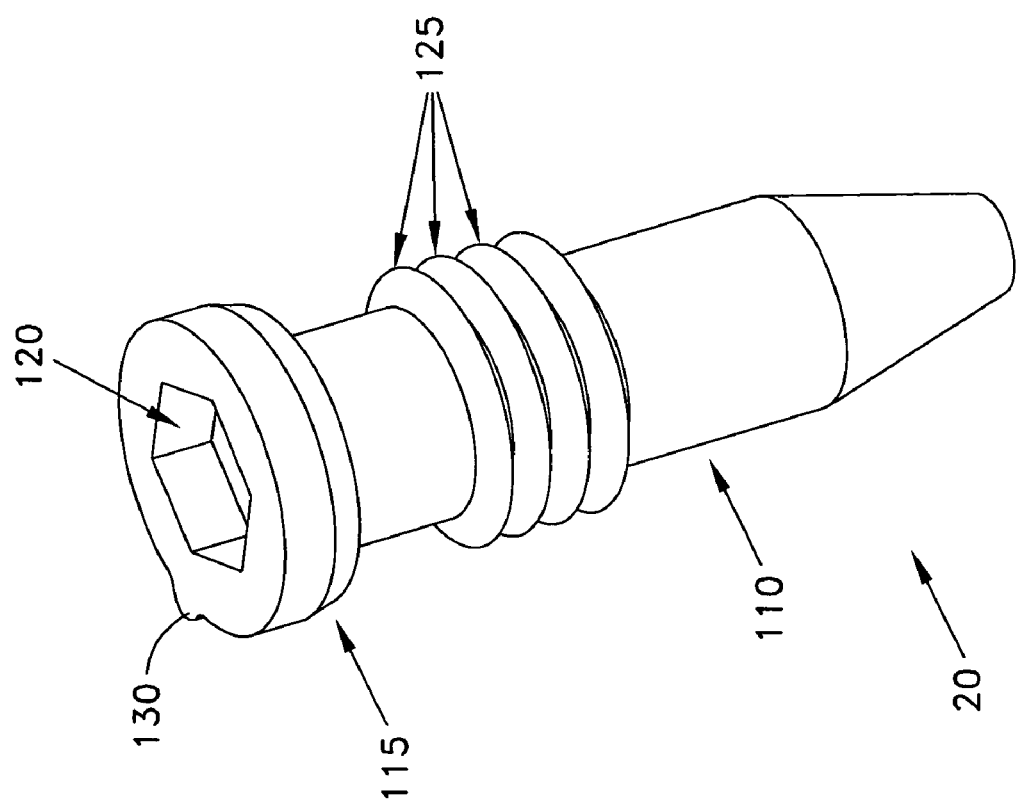
FIG. 29 is a schematic view showing another preferred form of the screw.

Also by way of example but not limitation, screw 20 may be sized to terminate within sleeve 15 rather than extend out the end of sleeve 15. Furthermore, the screw thread 125 of screw 20 might be replaced by ribs (or other lateral projections) 125 for engaging the interior side wall of sleeve 15. See, for example, FIG. 29, which shows such a ribbed construction. In this case, or in other cases, the interior side wall of sleeve 15 might not be threaded. Additionally, screw 20 can be cannulated, so as to facilitate delivery over a guidewire.

Furthermore, sleeve 15 might be formed without a counterbore, and screw 20 might be formed without an enlarged head, in which case the screw would essentially constitute a threaded pin to be seated within a sleeve bore.

Additionally, the positions of detent 105 and finger 130 may be reversed, i.e., finger 130 may be formed on sleeve 15 and detent 105 may be formed on screw 20. Additionally, more than one detent and/or finger may be provided, e.g., the apparatus may comprise one finger and multiple detents.

Also, screw 20 and sleeve 15 may be pre-assembled (either at the time or manufacture or in the operating room) so as to constitute a single unit.

It should also be appreciated that the present invention may be used to secure a rod (or the like) to bone. By way of example but not limitation, the rod could be a spinal rod (or other surgical rod) used to stabilize a plurality of vertebral bodies relative to one another. In this case, a portion of the rod might be modified so as to be analogous to plate 10 (e.g., so as to provide one or more openings 35 through the rod for receiving a sleeve 15 and screw 20). See FIG. 30, where a rod 141 is provided with one or more openings 35 therethrough. Where the rod has a relatively narrow diameter, and looking now at FIG. 31, a portion of rod 141 might be flattened and/or laterally expanded so as to provide an enlarged surface area 142 for receiving openings 35 to receive sleeve 15. However, where the rod has a relatively large diameter, openings 35 may be formed in the rod without requiring any flattening and/or lateral expansion of the rod.

Figure 32:
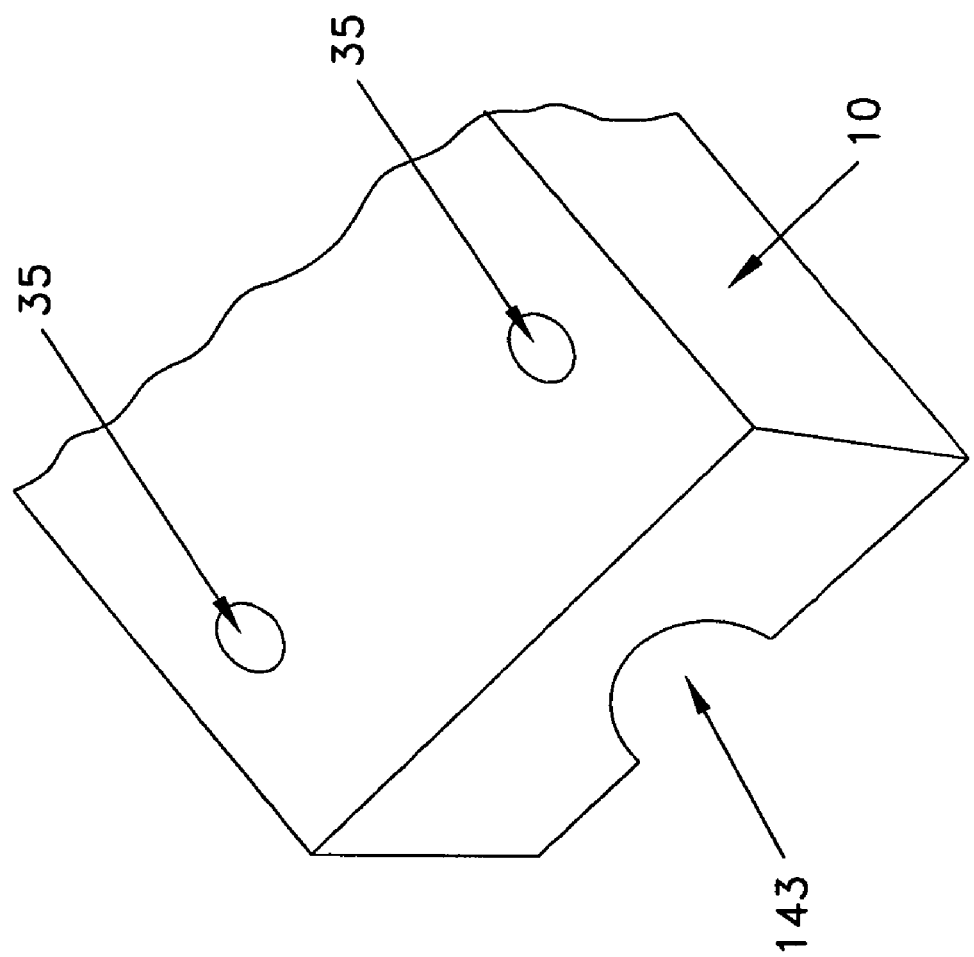
FIG. 32 is a schematic view of a plate for capturing a rod against bone.

Alternatively, an adapter might be provided to secure the rod to bone. In this case, and looking now at FIG. 32, plate 10 could function as a rod mount, preferably with a groove 143 on the underside of the plate to capture the rod to the bone. In this case, it may be necessary to position openings 35 in plate 10 so that a sleeve 15 passing through openings 35 pass alongside a rod captured in the groove. See FIG. 32.

Figure 33:
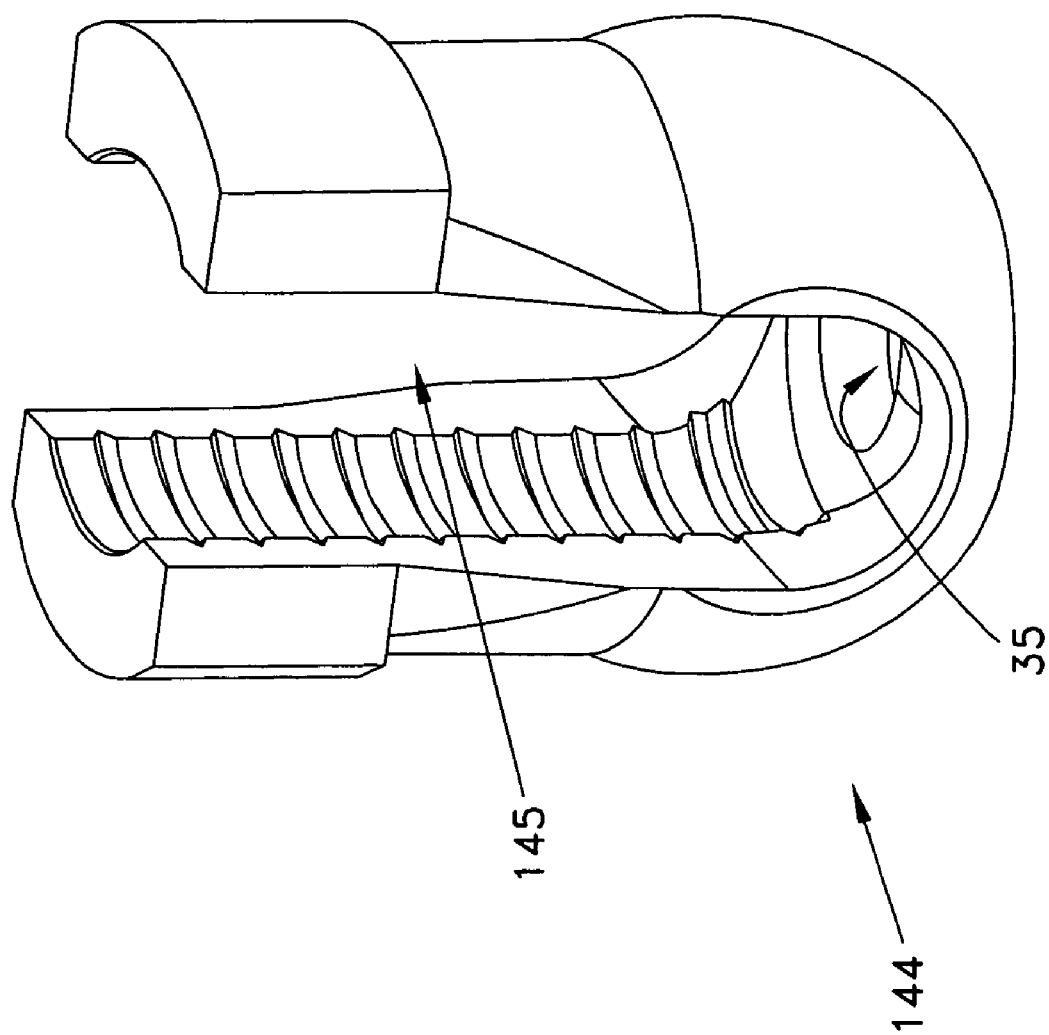
FIG. 33 is a schematic view of a "tulip" mount which may be secured to a bone using the sleeve/screw construction of the present invention.

Additionally, the novel sleeve/screw construction can be used to secure a tulip-shaped mount to the bone, with the tulip-shaped mount being used to secure a rod to the bone. More particularly, and looking now at FIG. 33, a tulip-shaped mount 144 is shown, wherein the tulip-shaped mount has an opening 35 for securing the tulip-shaped mount to bone and a slot 145 for receiving a rod.

Figure 34:
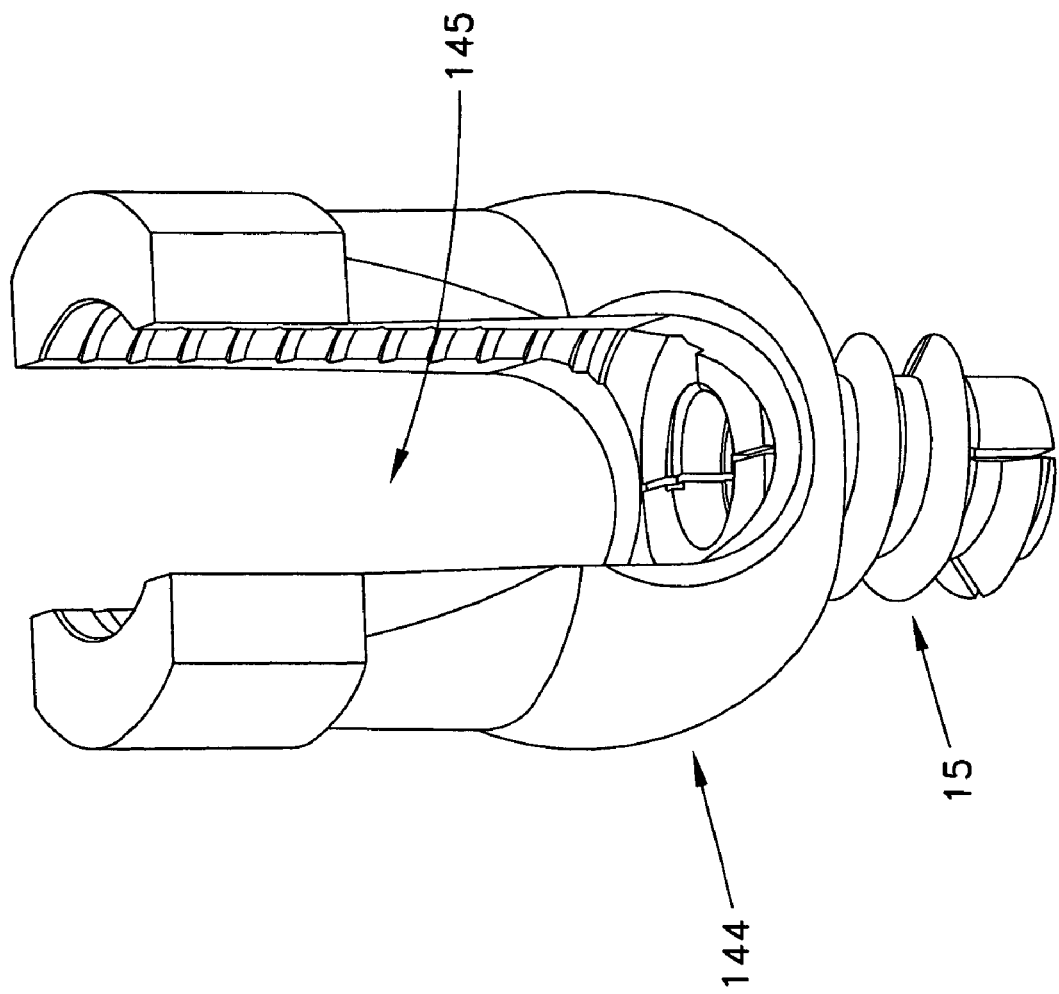
FIGS. 34 and 35 show the sleeve being mated with the tulip mount, and the screw being mated with the sleeve, respectively.
Figure 35:
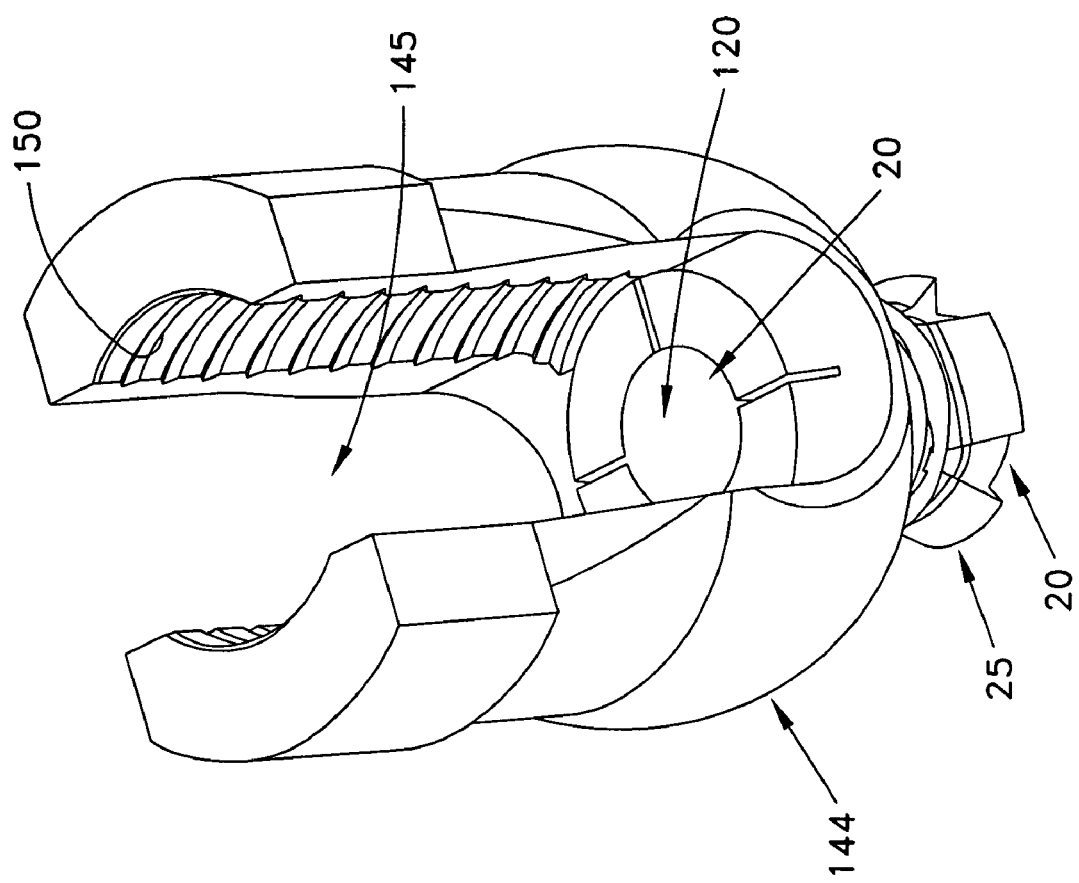

In use, tulip-shaped mount 144 is positioned alongside bone. A hole is drilled in the bone via opening 35 formed in tulip-shaped mount 144. Sleeve 15 is advanced through opening 35 (FIG. 34) and into the hole formed in the bone. Next, screw 20 is advanced through sleeve 15, causing sleeve 15 to be radially expanded, so that the sleeve is simultaneously secured to both the bone and to tulip-shaped mount 144 (see FIG. 35). With tulip-shaped mount 144 secured to the bone, a rod may be positioned in the slot 145 of tulip-shaped mount 144, whereby to stabilize the bone(s). If desired, tulip-shaped mount 144 may be provided with a threaded cap (not shown) which can be positioned superior to the rod using threads 150, so as to securely hold the rod in place within slot 145 of tulip-shaped mount 144.

Figure 36:
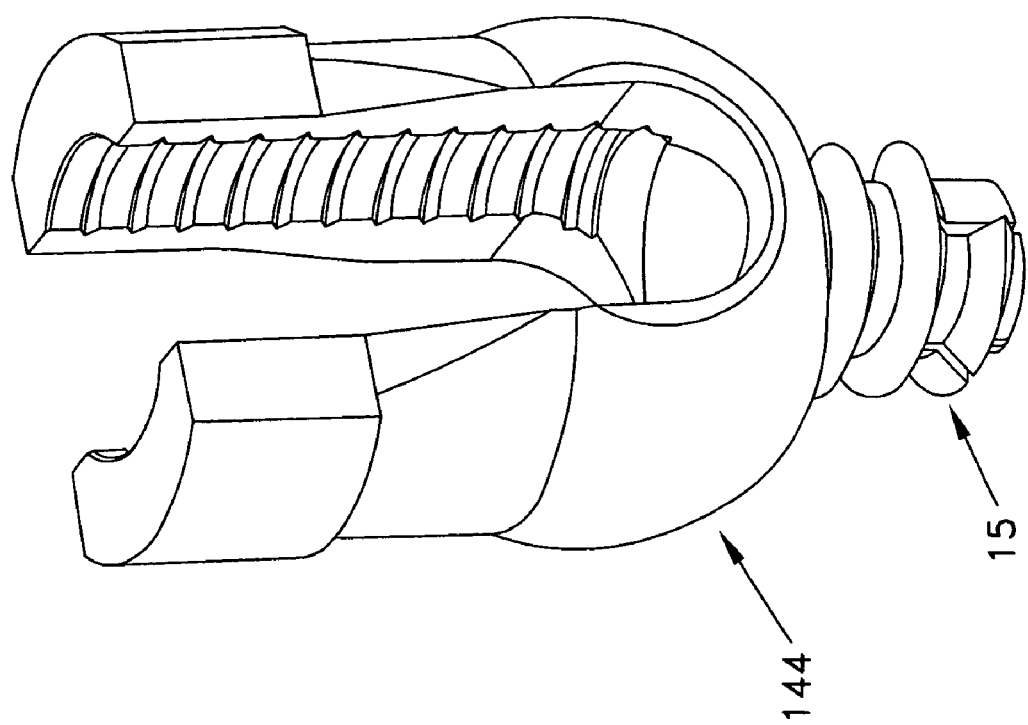
FIG. 36 is a schematic view showing a hybrid tulip mount/sleeve construction.
Figure 37:
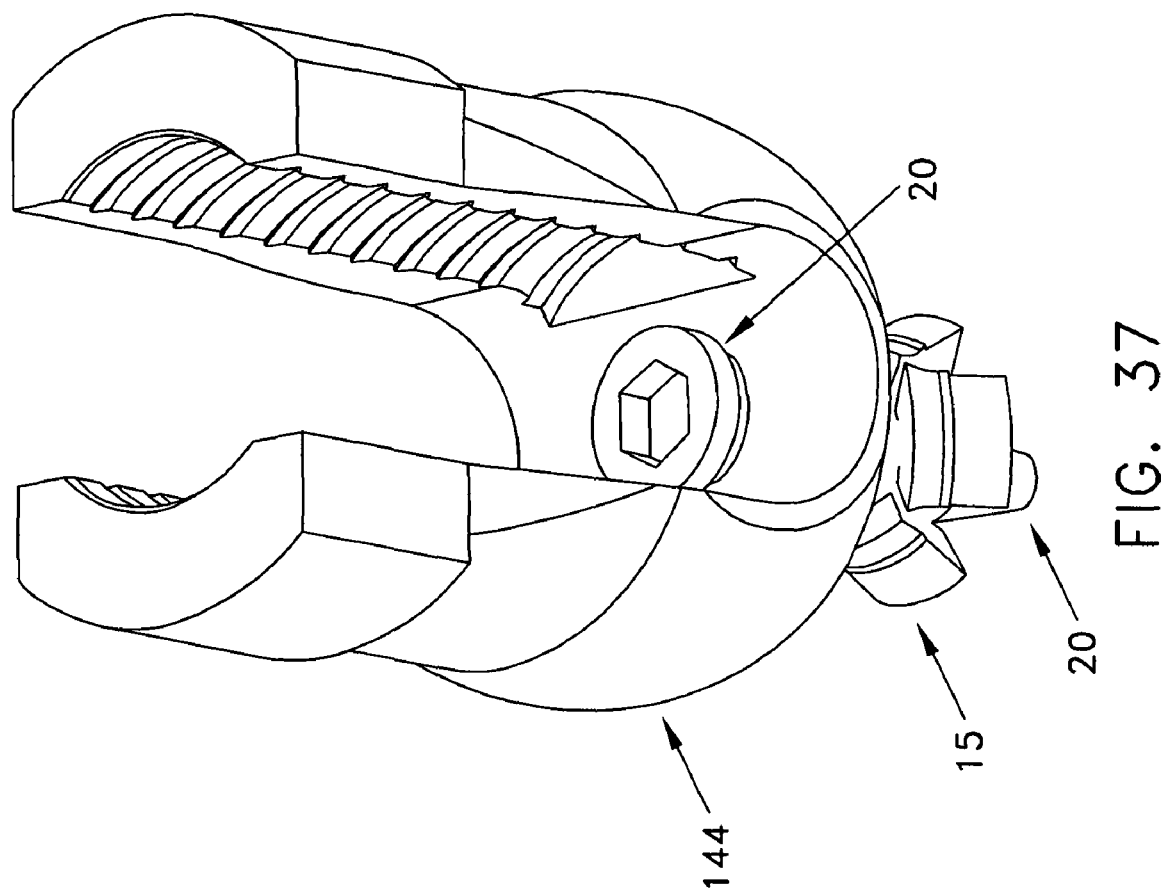
FIG. 37 is a schematic view showing a screw being mated with the hybrid tulip mount/sleeve construction shown in FIG. 36.

Looking next at FIGS. 36 and 37, it should also be appreciated that sleeve 15 can be formed integral with tulip-shaped mount 144.

Materials

The various components can be formed out of any material or materials consistent with the present invention. Thus, for example, some or all of the components may be formed out of implantable metals (e.g., surgical grade stainless steel, titanium, Nitinol, etc.), implantable plastics, implantable absorbables, etc.

Modifications

It will be understood that many changes in the details, materials, steps and arrangements of parts, which have been herein described and illustrated in order to explain the nature of the invention, may be made by those skilled in the art without departing from the principles and scope of the present invention.

What is claimed is:

1. A surgical system comprising:
an object to be secured to bone, the object comprising an opening extending therethrough; and
a sleeve/screw construction for securing the object to bone, the sleeve/screw construction comprising:
a sleeve adapted for positioning through the opening in the object and into the bone, the sleeve comprising:
a shank having a distal end and a proximal end and an opening extending from the distal end to the proximal end, wherein the opening narrows toward the distal end of the shank, and further wherein the distal end of the shank is slit so as to form a plurality of radially-expandable segments; and
an enlarged head formed at the proximal end of the shank, the enlarged head being formed so as to be radially-expandable;
the sleeve being sized so that when the sleeve is positioned through the opening in the object and into the bone, at least a portion of the radially-expandable segments extend into the bone beyond the cortical bone/cancellous bone interface; and
a screw adapted for positioning through the opening in the sleeve, the screw being sized so as to (i) radially expand the distal end of the sleeve so that the sleeve is secured to the bone, and (ii) radially expand the enlarged head of the sleeve so that the sleeve is secured to the object, whereby to secure the object to the bone;
wherein the opening in the object and the enlarged head of the sleeve are formed with non-circular shapes so as to provide an anti-rotation contact between the sleeve and the object.

2. A system according to claim 1 wherein the object comprises a plate.

3. A system according to claim 2 wherein the plate comprises a fracture fixation plate, and further wherein the plate comprises a plurality of openings extending through the plate, the openings being spaced from one another so that at least one opening is disposed on either side of a fracture line.

4. A system according to claim 1 wherein the opening comprises a bore/counterbore construction, and further wherein the bore is configured to receive the shank of the sleeve and the counterbore is configured to receive the enlarged head of the sleeve.

5. A system according to claim 1 wherein a raised rim is disposed about the opening in the object.

6. A system according to claim 1 wherein the opening in the object has a slot-like configuration so as to allow a degree of longitudinal freedom when positioning the sleeve through the opening.

7. A system according to claim 1 wherein the opening in the object and the sleeve are sized and shaped so as to permit the sleeve to be placed through the opening in the object at an acute angle relative to the longitudinal axis of the object.

8. A system according to claim 1 wherein the sleeve has a screw thread formed on the exterior surface of the shank.

9. A system according to claim 1 wherein the sleeve has at least one rib formed on the exterior surface of the shank.

10. A system according to claim 9 wherein the at least one rib has a sloped leading edge so as to facilitate insertion and a sharp trailing rim so as to retard withdrawal.

11. A system according to claim 1 wherein the screw is replaced by a ribbed pin.

12. A system according to claim 1 wherein the enlarged head of the sleeve comprises a plurality of radially-extending slots, whereby to facilitate radial expansion of the enlarged head of the sleeve when the screw is disposed in the sleeve.

13. A system according to claim 1 wherein the sleeve comprises a detent at the proximal end of the opening in the sleeve, and further wherein the screw comprises a radially-extending finger at the proximal end thereof, the finger being received in the detent so as to releasably lock the screw to the sleeve.

14. A surgical system comprising:
an object to be secured to bone, the object comprising an opening extending therethrough; and
a sleeve/screw construction for securing the object to bone, the sleeve/screw construction comprising:
a sleeve adapted for positioning through the opening in the object and into the bone, the sleeve comprising:
a shank having a distal end and a proximal end and an opening extending from the distal end to the proximal end, wherein the opening narrows toward the distal end of the shank, and further wherein the distal end of the shank is slit so as to form a plurality of radially-expandable segments; and
an enlarged head formed at the proximal end of the shank, the enlarged head being formed so as to be radially-expandable;
the sleeve being sized so that when the sleeve is positioned through the opening in the object and into the bone, at least a portion of the radially-expandable segments extend into the bone beyond the cortical bone/cancellous bone interface; and
a screw adapted for positioning through the opening in the sleeve, the screw being sized so as to (i) radially expand the distal end of the sleeve so that the sleeve is secured to the bone, and (ii) radially expand the enlarged head of the sleeve so that the sleeve is secured to the object, whereby to secure the object to the bone;
wherein the plate has a groove on the underside thereof, the groove being sized to seat a rod therein and thereby capture the rod against the bone when the plate is secured to the bone.

15. A surgical system comprising:
an object to be secured to bone, the object comprising an opening extending therethrough; and
a sleeve/screw construction for securing the object to bone, the sleeve/screw construction comprising:
a sleeve adapted for positioning through the opening in the object and into the bone, the sleeve comprising:
a shank having a distal end and a proximal end and an opening extending from the distal end to the proximal end, wherein the opening narrows toward the distal end of the shank, and further wherein the distal end of the shank is slit so as to form a plurality of radially-expandable segments; and an enlarged head formed at the proximal end of the shank, the enlarged head being formed so as to be radially-expandable;

the sleeve being sized so that when the sleeve is positioned through the opening in the object and into the bone, at least a portion of the radially-expandable segments extend into the bone beyond the cortical bone/cancellous bone interface; and a screw adapted for positioning through the opening in the sleeve, the screw being sized so as to (i) radially expand the distal end of the sleeve so that the sleeve is secured to the bone, and (ii) radially expand the enlarged head of the sleeve so that the sleeve is secured to the object, whereby to secure the object to the bone;

wherein the object comprises a rod.

16. A system according to claim 15 wherein the rod has a laterally-expanded region adjacent the opening.

17. A surgical system comprising:

an object to be secured to bone, the object comprising an opening extending therethrough; and a sleeve/screw construction for securing the object to bone, the sleeve/screw construction comprising:

a sleeve adapted for positioning through the opening in the object and into the bone, the sleeve comprising:

a shank having a distal end and a proximal end and an opening extending from the distal end to the proximal end, wherein the opening narrows toward the distal end of the shank, and further wherein the distal end of the shank is slit so as to form a plurality of radially-expandable segments; and an enlarged head formed at the proximal end of the shank, the enlarged head being formed so as to be radially-expandable;

the sleeve being sized so that when the sleeve is positioned through the opening in the object and into the bone, at least a portion of the radially-expandable segments extend into the bone beyond the cortical bone/cancellous bone interface; and a screw adapted for positioning through the opening in the sleeve, the screw being sized so as to (i) radially expand the distal end of the sleeve, so that the sleeve is secured to the bone, and (ii) radially expand the enlarged head of the sleeve so that the sleeve is secured to the object, whereby to secure the object to the bone;

wherein the object comprises a tulip-shaped mount for receiving a rod therein.

18. A surgical system comprising:

an object to be secured to bone, the object comprising an opening extending therethrough; and a sleeve/expander construction for securing the object to bone, the sleeve/expander construction comprising:

a sleeve adapted for positioning through the opening in the object and into the bone, the sleeve comprising:

a shank having a distal end and a proximal end and an opening extending from the distal end to the proximal end, wherein the opening narrows toward the distal end of the shank, and further wherein the distal end of the shank is slit so as to form a plurality of radially-expandable segments; and an enlarged head formed at the proximal end of the shank, the enlarged head being formed so as to be radially-expandable; and an expander adapted for positioning through the opening in the sleeve, the expander being sized so as to (i) radially expand the distal end of the sleeve so that the sleeve is secured to the bone, and (ii) radially expand the enlarged head of the sleeve so that the sleeve is secured to the object, whereby to secure the object to the bone;

wherein the opening in the object and the enlarged head of the sleeve are formed with non-circular shapes so as to provide an anti-rotation contact between the sleeve and the object.

19. A system according to claim 18 wherein the expander comprises a screw.

20. A system according to claim 18 wherein the expander comprises a ribbed pin.

21. A system according to claim 18 wherein the sleeve is sized so that when the sleeve is positioned through the opening in the object and into the bone, at least a portion of the radially-expandable segments extend into the bone beyond the cortical bone/cancellous bone interface.

22. A method for securing an object to bone, the method comprising the steps of:

providing an object having an opening extending therethrough, and providing a sleeve/expander construction for securing the object to bone, the sleeve/expander construction comprising:

a sleeve adapted for positioning through the opening in the object and into the bone, the sleeve comprising:

a shank having a distal end and a proximal end and an opening extending from the distal end to the proximal end, wherein the opening narrows toward the distal end of the shank, and further wherein the distal end of the shank is slit so as to form a plurality of radially-expandable segments; and an enlarged head formed at the proximal end of the shank, the enlarged head being formed so as to be radially-expandable;

wherein the opening in the object and the enlarged head of the sleeve are formed with non-circular shapes so as to provide an anti-rotation contact between the sleeve and the object; and an expander adapted for positioning through the opening in the sleeve, the expander being sized so as to (i) radially expand the distal end of the sleeve so that the sleeve is secured to the bone, and (ii) radially expand the enlarged head of the sleeve so that the sleeve is secured to the object, whereby to secure the object to the bone;

positioning the object against the bone;

placing the sleeve through the opening in the object and into the bone; and positioning the screw in the sleeve so as to secure the sleeve to the bone and to the object, whereby to secure the object to the bone.

* * * * *